US010882911B2

(12) United States Patent
Park et al.

(10) Patent No.: US 10,882,911 B2
(45) Date of Patent: Jan. 5, 2021

(54) CD40L BINDING POLYPEPTIDE

(71) Applicant: SEOUL NATIONAL UNIVERSITY R&DB FOUNDATION, Seoul (KR)

(72) Inventors: SeongHoe Park, Seoul (KR); Kyeong Cheon Jung, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 253 days.

(21) Appl. No.: 15/739,560

(22) PCT Filed: Jun. 22, 2016

(86) PCT No.: PCT/KR2016/006589
§ 371 (c)(1),
(2) Date: Dec. 22, 2017

(87) PCT Pub. No.: WO2016/208948
PCT Pub. Date: Dec. 29, 2016

(65) Prior Publication Data
US 2018/0194847 A1 Jul. 12, 2018

(30) Foreign Application Priority Data

Jun. 23, 2015 (KR) ........................ 10-2015-0088819
Jun. 21, 2016 (KR) ........................ 10-2016-0077311

(51) Int. Cl.
| | |
|---|---|
| A61K 39/395 | (2006.01) |
| C07K 16/28 | (2006.01) |
| A61P 7/00 | (2006.01) |
| A61P 37/06 | (2006.01) |
| A61K 39/00 | (2006.01) |
| C07K 16/46 | (2006.01) |

(52) U.S. Cl.
CPC ...... *C07K 16/2875* (2013.01); *A61K 39/0008* (2013.01); *A61K 39/395* (2013.01); *A61P 7/00* (2018.01); *A61P 37/06* (2018.01); *C07K 16/461* (2013.01); *A61K 2039/505* (2013.01); *C07K 2317/24* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2005/0181994 A1* | 8/2005 | Chamberlain ....... | C07K 14/525 424/85.1 |
| 2008/0305116 A1* | 12/2008 | Van Vlijmen ..... | C07K 16/2875 424/172.1 |
| 2014/0093497 A1 | 4/2014 | Reimann et al. | |
| 2015/0098955 A1* | 4/2015 | Coyle .................... | A61P 19/00 424/185.1 |

OTHER PUBLICATIONS

An et al., Journal of Biological Chemistry 286: 11226-11235 (2011). (Year: 2011).*
Rudikoff et al. Proc Natl Acad Sci USA 79: 1979-1983 (1982) . (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14: 2784-2794 (1995). (Year: 1995).*
D'Angelo et al., Many Routes to an Antibody Heavy-Chain CDR3: Necessary, Yet Insufficient, for Specific Binding, Frontiers in Immunology vol. 9, Article 395 Mar. 2018; doi:10.3389/fimmu.2018. 00395. (Year: 2018).*
Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/ 10.1080/19420862.2017.1389355. (Year: 2018).*
Vonderheide et al., Clin Cancer Res 19: 1035-1043 (2013). (Year: 2013).*
Jefferis, Nature Reviews / Drug Discovery 8: 226-234 (Mar. 2009). (Year: 2009).*
Barnes et al., "Advances in animal cell recombinant protein production: GS-NS0 expression system", Cytotechnology, vol. 32, pp. 109-123, (2000).
Bartelds et al., "Development of Antidrug Antibodies Against Adalimumab and Association With Disease Activity and Treatment Failure During Long-term Follow-up", JAMA, vol. 305, No. 14, pp. 1460-1468, (2011).
Boumpas et al., "A Short Course of BG9588 (Anti-CD40 Ligand Antibody) Improves Serologic Activity and Decreases Hematuria in Patients With Proliferative Lupus Glomerulonephritis", Arthritis & Rheumatism, vol. 48, No. 3, pp. 719-727, (2003).
Chirmule et al., "Immunogenicity to Therapeutic Proteins: Impact on PK/PD and Efficacy", The AAPS Journal, vol. 14, No. 2, pp. 296-302, (2012).
Durie et al., "Prevention of Collagen-Induced Arthritis with an Antibody to gp39, the Ligand for CD40", Science, vol. 261, pp. 1328-1330, (1993).
Kaufman, "Overview of Vector Design for Mammalian Gene Expression", Molecular Biotechnology, vol. 16, pp. 151-160, (2000).
Kelsoe, "Therapeutic CD154 antibody for lupus: promise for the future?" J. Clin. Invest., vol. 112, pp. 1480-1482, (2003).
Kirk et al., "Treatment with humanized monoclonal antibody against CD154 prevents acute renal allograft rejection in nonhuman primates", Nature Medicine, vol. 5, No. 6, pp. 686-693, (1999).
Kirk et al., "The role of CD154 in organ transplant rejection and acceptance", Phil. Trans. R. Soc. Lond. B, vol. 356, pp. 691-702, (2001).
Kohler et al., "Continuous cultures of fused cells secreting antibody of predefined specificity", Nature, vol. 256, pp. 495-497, (1975).

(Continued)

*Primary Examiner* — Phillip Gambel
(74) *Attorney, Agent, or Firm* — Vorys, Sater, Seymour and Pease LLP; Mih Suhn Koh

(57) ABSTRACT

Disclosed is a CD154 binding polypeptide that specifically recognizes CD154. The polypeptide according to the present disclosure effectively inhibits the CD154-CD40 interaction without activating platelets, and thus can be effectively used in the prevention or treatment of various T cell-mediated or antibody-mediated diseases or symptoms, which requires inhibition of the interaction.

16 Claims, 4 Drawing Sheets

Specification includes a Sequence Listing.

(56) References Cited

OTHER PUBLICATIONS

Kuwana et al., "Effect of a single injection of humanized anti-CD154 monoclonal antibody on the platelet-specific autoimmune response in patients with immune thrombocytopenic purpura", Blood, vol. 103, pp. 1229-1236, (2004).
Morrison et al., "Chimeric human antibody molecules: Mouse antigen-binding domains with human constant region domains", Proc. Natl. Acad. Sci. USA, vol. 81, pp. 6851-6855, (1984).
Nagelkerken et al., "FcR Interactions Do Not Play a Major Role in Inhibition of Experimental Autoimmune Encephalomyelitis by Anti-CD154 Monoclonal Antibodies", The Journal of Immunology, vol. 173, pp. 993-999, (2004).
Norderhaug et al., "Versatile vectors for transient and stable expression of recombinant antibody molecules in mammalian cells", Journal of Immunological Methods, vol. 204, pp. 77-87, (1997).
Riechmann et al., "Reshaping human antibodies for therapy", Nature, vol. 332, pp. 323-327, (1988).
Schlaeger, "The protein hydrolysate, Primatone RL, is a cost-effective multiple growth promoter of mammalian cell culture in serum-containing and serum-free media and displays anti-apoptosis properties", Journal of Immunological Methods, vol. 194, pp. 191-199, (1996).
Schuler et al., "Efficacy and Safety of ABI793, A Novel Human Anti-Human CD154 Monoclonal Antibody, in Cynomolgus Monkey Renal Allotransplantation", Transplantation, vol. 77, No. 5, pp. 717-726, (2004).
Seung et al., "Allogeneic hematopoietic chimerism in mice treated with sublethal myeloablation and anti-CD154 antibody: absence of graft-versus-host disease, induction of skin allograft tolerance, and prevention of recurrent autoimmunity in islet-allografted NOD/Lt mice", Blood, vol. 95, pp. 2175-2182, (2000).

\* cited by examiner

[FIG. 1]
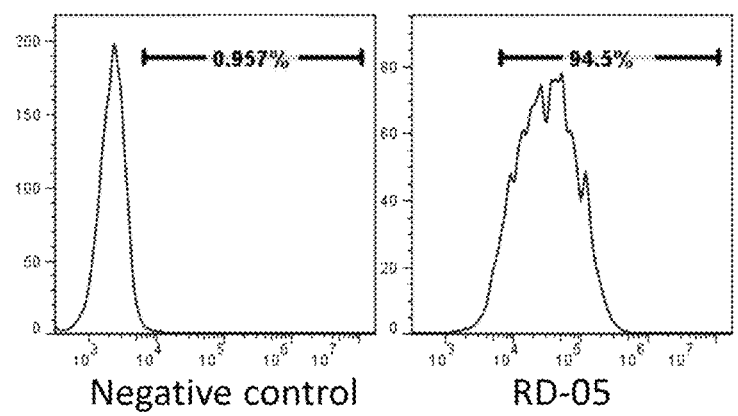
[FIG. 2]
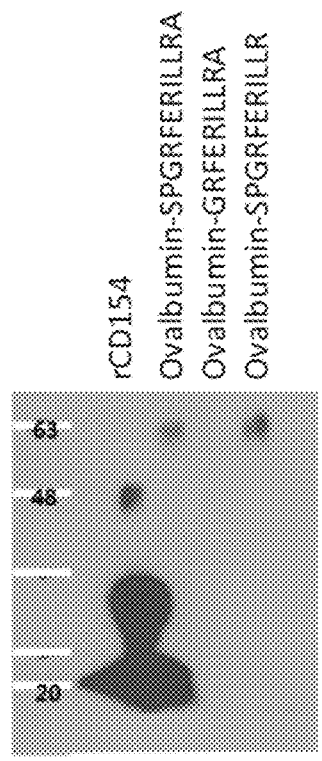

[FIG. 3]
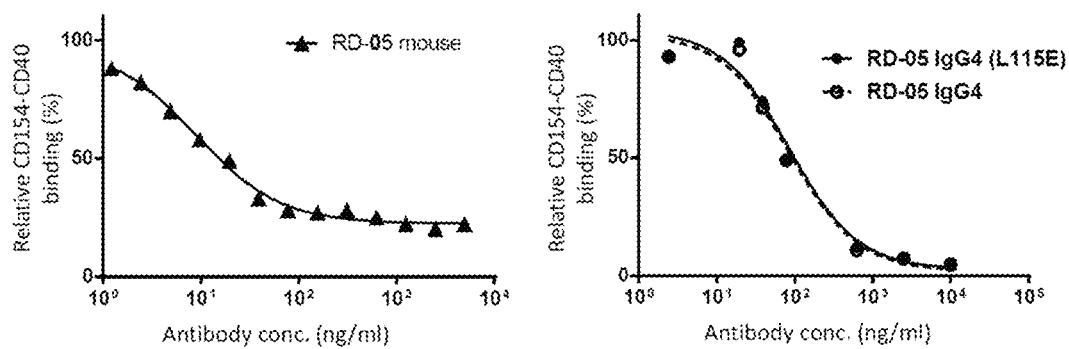
[FIG. 4]
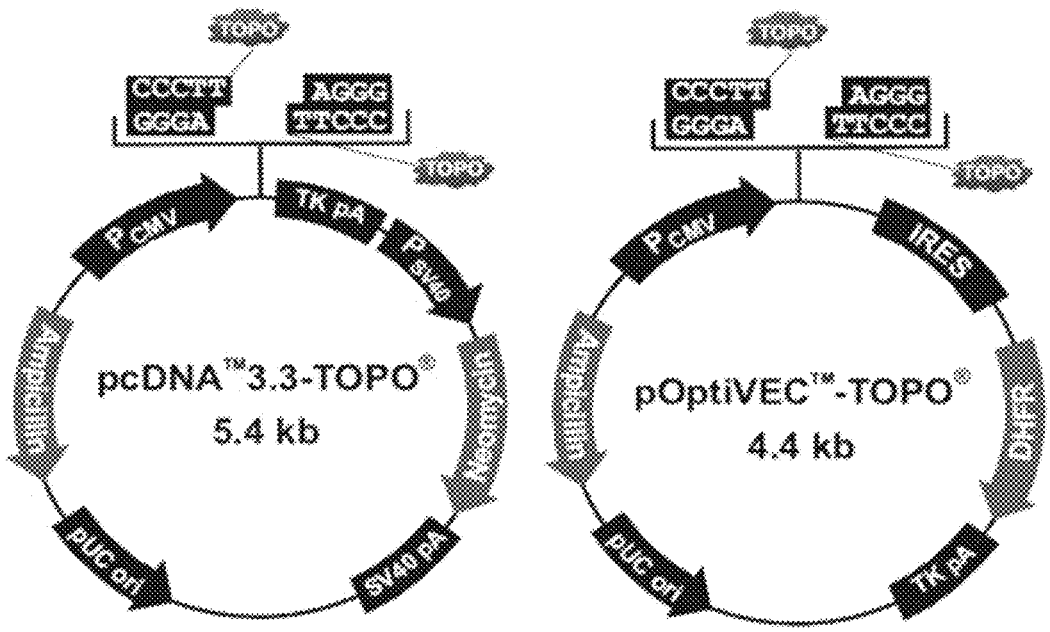

[FIG. 5]
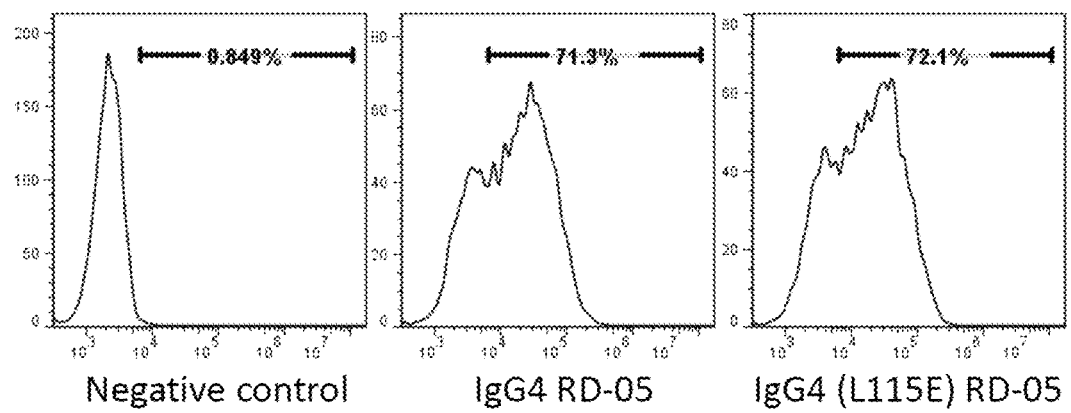
[FIG. 6]
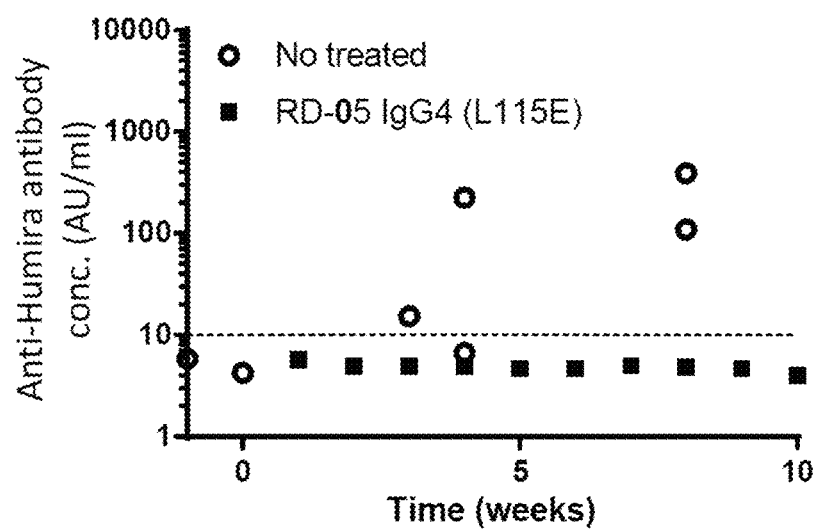

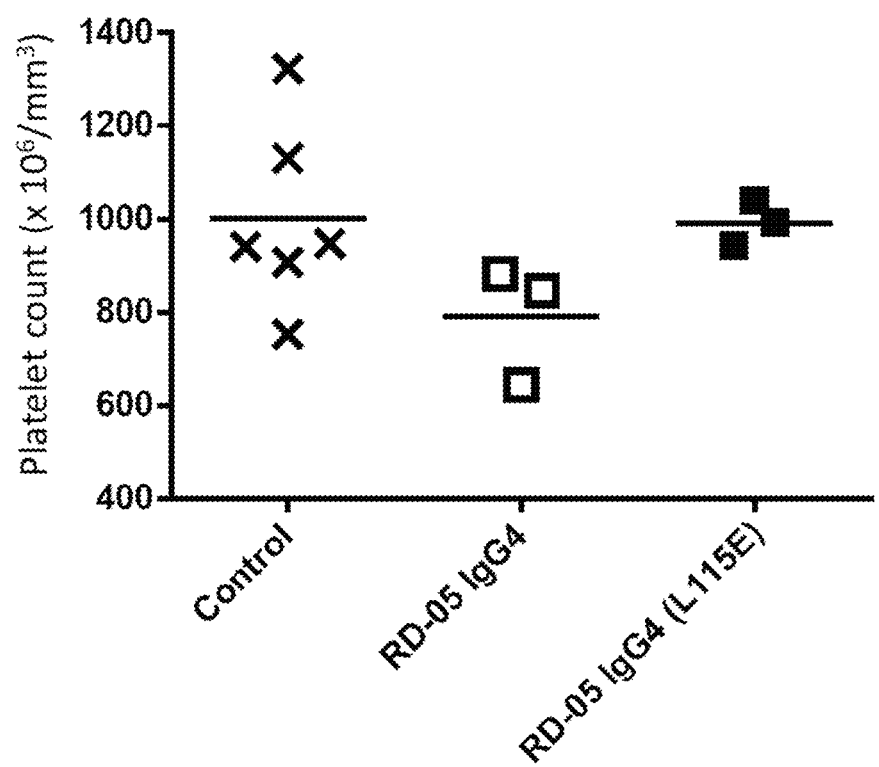
[FIG. 7]

SEQUENCE LISTING

```
<160> NUMBER OF SEQ ID NOS: 47

<210> SEQ ID NO 1
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: HCDR1 of RD05

<400> SEQUENCE: 1

Gly Tyr Ser Ile Thr Ser Asp Tyr Ala
1               5

<210> SEQ ID NO 2
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: HCDR2 of RD05

<400> SEQUENCE: 2

Ile Thr Tyr Ser Gly Thr Thr
1               5

<210> SEQ ID NO 3
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: HCDR3 of RD05

<400> SEQUENCE: 3

Ala Arg Ser Pro Tyr Tyr Gly Pro Trp Tyr Phe Asp Val
1               5                   10

<210> SEQ ID NO 4
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: LCDR1 of RD05

<400> SEQUENCE: 4

Gln Ser Val Asp Tyr Asp Gly Asp Ser Tyr
1               5                   10

<210> SEQ ID NO 5
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: LCDR2 of RD05

<400> SEQUENCE: 5

Ala Ala Ser
1
```

```
<210> SEQ ID NO 6
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LCDR3 of RD05

<400> SEQUENCE: 6

Gln Gln Ser Asn Glu Asp Pro
1               5

<210> SEQ ID NO 7
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Heavy chain variable region of RD-05

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Thr Thr Ser Tyr Asn Pro Ser Leu
    50                  55                  60

Lys Ser Arg Ile Ser Leu Thr Arg Asp Thr Ser Lys Asn Gln Phe Phe
65                  70                  75                  80

Leu Gln Leu Asn Ala Val Thr Thr Glu Asp Thr Ala Thr Tyr Tyr Cys
                85                  90                  95

Ala Arg Ser Pro Tyr Tyr Gly Pro Trp Tyr Phe Asp Val Trp Gly Ala
            100                 105                 110

Gly Thr Thr Val Thr Val Ser Ser
        115                 120

<210> SEQ ID NO 8
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Light chain variable region of RD-05

<400> SEQUENCE: 8

Asp Ile Val Leu Thr Gln Ser Pro Ala Ser Leu Thr Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu His Trp Tyr Gln Gln Lys Pro Gly Gln Pro Pro
            35                  40                  45

Lys Leu Leu Ile Tyr Ala Ala Ser Tyr Leu Glu Ser Gly Ile Pro Ala
    50                  55                  60

Arg Phe Ser Gly Ser Gly Ser Gly Thr Asp Phe Thr Leu Asn Ile His
65                  70                  75                  80
```

Pro Val Glu Glu Glu Asp Ala Ala Thr Tyr Tyr Cys Gln Gln Ser Asn
                    85                  90                  95

Glu Asp Pro Asn Thr Phe Gly Gly Gly Thr Lys Leu Glu Ile Lys Arg
            100                 105                 110

<210> SEQ ID NO 9
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Human IgG4 Heavy chain constant region

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 327
<212> TYPE: PRT
<213> ORGANISM: Artificial Sequence
<220> FEATURE:
<223> OTHER INFORMATION: Human IgG4 HC with sub at 115 with Glu

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

```
<210> SEQ ID NO 11
<211> LENGTH: 106
<212> TYPE: PRT
<213> ORGANISM: Homo sapiens
<220> FEATURE:
<221> NAME/KEY: MISC_FEATURE
<222> LOCATION: (1)..(106)
<223> OTHER INFORMATION: Human IgG4 kappa Light chain constant region

<400> SEQUENCE: 11

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 12
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: epitope of anti-CD154

<400> SEQUENCE: 12

Ser Pro Gly Arg Phe Glu Arg Ile Leu Leu Arg Ala
1               5                   10

<210> SEQ ID NO 13
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: epitope of anti-CD154

<400> SEQUENCE: 13

Ser Pro Gly Arg Phe Glu Arg Ile Leu Leu Arg
1               5                   10

<210> SEQ ID NO 14
<211> LENGTH: 27
<212> TYPE: DNA
<213> ORGANISM: Mus musculus
<220> FEATURE:
<221> NAME/KEY: MISC_FEATURE
<222> LOCATION: (1)..(27)
<223> OTHER INFORMATION: HCDR1 DNA sequence of RD05

<400> SEQUENCE: 14
ggctattcaa ttacctccga ctacgcc                                           27
```

```
<210> SEQ ID NO 15
<211> LENGTH: 21
<212> TYPE: DNA
<213> ORGANISM: Mus musculus
<220> FEATURE:
<221> NAME/KEY: MISC_FEATURE
<222> LOCATION: (1)..(21)
<223> OTHER INFORMATION: HCDR2 DNA sequence of RD05

<400> SEQUENCE: 15
ataacttata gcggaaccac a                                             21

<210> SEQ ID NO 16
<211> LENGTH: 39
<212> TYPE: DNA
<213> ORGANISM: Mus musculus
<220> FEATURE:
<221> NAME/KEY: MISC_FEATURE
<222> LOCATION: (1)..(39)
<223> OTHER INFORMATION: HCDR3 DNA sequence of RD05

<400> SEQUENCE: 16
gccagaagcc cctactatgg gccctggtac ttcgatgta                           39

<210> SEQ ID NO 17
<211> LENGTH: 360
<212> TYPE: DNA
<213> ORGANISM: Mus musculus
<220> FEATURE:
<221> NAME/KEY: MISC_FEATURE
<222> LOCATION: (1)..(360)
<223> OTHER INFORMATION: Heavy chain variable region DNA sequence of
      RD-05

<400> SEQUENCE: 17
gatgtgcagc ttcaggagag cggcccaggc ctggtgaagc cttctcagag tctgtccctc    60
acttgtaccg tgaccggcta ttcaattacc tccgactacg cctggaattg gatccggcaa   120
ttcccaggca acaagctgga gtggatgggt tatataactt atagcggaac acatccctac   180
aaccccagtc tcaagagccg aatctcacta acacgcgaca catccaaaaa tcagttcttt   240
ctgcagttga acgctgtcac tactgaagac accgccacat actactgcgc cagaagcccc   300
tactatgggc cctggtactt cgatgtatgg ggagcaggga ccacggttac cgtctcatct   360

<210> SEQ ID NO 18
<211> LENGTH: 30
<212> TYPE: DNA
<213> ORGANISM: Mus musculus
<220> FEATURE:
<221> NAME/KEY: MISC_FEATURE
<222> LOCATION: (1)..(30)
<223> OTHER INFORMATION: LCDR1 DNA sequence of RD05

<400> SEQUENCE: 18
caaagtgtag actatgacgg cgattcctat                                    30

<210> SEQ ID NO 19
<211> LENGTH: 9
<212> TYPE: DNA
<213> ORGANISM: Mus musculus
<220> FEATURE:
<221> NAME/KEY: MISC_FEATURE
<222> LOCATION: (1)..(9)
<223> OTHER INFORMATION: LCDR2 DNA sequence of RD05

<400> SEQUENCE: 19 gctgcaagc                                                            9
```

```
<210> SEQ ID NO 20
<211> LENGTH: 20
<212> TYPE: DNA
<213> ORGANISM: Mus musculus
<220> FEATURE:
<221> NAME/KEY: MISC_FEATURE
<222> LOCATION: (1)..(20)
<223> OTHER INFORMATION: LCDR3 DNA sequence of RD05

<400> SEQUENCE: 20
aacagagtaa tgaagatcct                                              20

<210> SEQ ID NO 21
<211> LENGTH: 336
<212> TYPE: DNA
<213> ORGANISM: Mus musculus
<220> FEATURE:
<221> NAME/KEY: MISC_FEATURE
<222> LOCATION: (1)..(336)
<223> OTHER INFORMATION: Light chain variable region DNA sequence of
      RD-05

<400> SEQUENCE: 21
gacattgtcc tgacccagtc accagcttct ctcactgtgt ctctggggca gagggccacc    60
atcagctgca aggccagcca aagtgtagac atgacggcg attcctattt gcactggtac   120
cagcagaaac ctggtcagcc ccccaagctt ctcatatacg ctgcaagcta tttagagtct   180
ggtatcccag ccagattcag tggctcagga tccggtacag atttcaccct caatatccat   240
cctgtggagg aggaagatgc tgcaacctac tactgtcaac agagtaatga agatcctaac   300
acgtttggcg gcgggactaa gctggaaatt aaacgg                            336

<210> SEQ ID NO 22
<211> LENGTH: 261
<212> TYPE: PRT
<213> ORGANISM: Homo sapiens
<220> FEATURE:
<221> NAME/KEY: MISC_FEATURE
<222> LOCATION: (1)..(261)
<223> OTHER INFORMATION: CD 40 Ligand

<400> SEQUENCE: 22

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160
```

Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
        180                 185                 190

Leu Cys Leu Lys Ser Pro Gly Arg Phe Glu Arg Ile Leu Leu Arg Ala
    195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 23
<211> LENGTH: 35
<212> TYPE: DNA
<213> ORGANISM: Artificial Sequence
<220> FEATURE:
<223> OTHER INFORMATION: MuIgVH5'-F

<400> SEQUENCE: 23
actagtcgac atgaacttyg ggytsagmtt grttt                              35

<210> SEQ ID NO 24
<211> LENGTH: 34
<212> TYPE: DNA
<213> ORGANISM: Artificial Sequence
<220> FEATURE:
<223> OTHER INFORMATION: MuIgGVH3'-2

<400> SEQUENCE: 24
cccaagcttc cagggrccar kggataracg rtgg                               34

<210> SEQ ID NO 25
<211> LENGTH: 39
<212> TYPE: DNA
<213> ORGANISM: Artificial Sequence
<220> FEATURE:
<223> OTHER INFORMATION: RD-05 VH region forward primer

<400> SEQUENCE: 25
ctcgagatga gggtgttaat tcttttgtgg ctgtttaca                          39

<210> SEQ ID NO 26
<211> LENGTH: 39
<212> TYPE: DNA
<213> ORGANISM: Artificial Sequence
<220> FEATURE:
<223> OTHER INFORMATION: RD-05 VH region reverse primer

<400> SEQUENCE: 26
gcccttggtg gaagcagatg agacggtaac cgtggtccc                          39

<210> SEQ ID NO 27
<211> LENGTH: 33
<212> TYPE: DNA
<213> ORGANISM: Artificial Sequence
<220> FEATURE:
<223> OTHER INFORMATION: MuIgkVL5'-B

```
<400> SEQUENCE: 27
gggaattcat ggagacagac acactcctgc tat                                33

<210> SEQ ID NO 28
<211> LENGTH: 30
<212> TYPE: DNA
<213> ORGANISM: Artificial Sequence
<220> FEATURE:
<223> OTHER INFORMATION: MuIgkVL3'-1

<400> SEQUENCE: 28
cccaagctta ctggatggtg ggaagatgga                                    30

<210> SEQ ID NO 29
<211> LENGTH: 39
<212> TYPE: DNA
<213> ORGANISM: Artificial Sequence
<220> FEATURE:
<223> OTHER INFORMATION: RD-05 VL region forward primer

<400> SEQUENCE: 29
ctcgagatgg agacagatac acttttgcta tgggttctg                          39

<210> SEQ ID NO 30
<211> LENGTH: 40
<212> TYPE: DNA
<213> ORGANISM: Artificial Sequence
<220> FEATURE:
<223> OTHER INFORMATION: RD-05 VL region reverse primer

<400> SEQUENCE: 30
ctggtgccgc cacagtccgt ttaatttcca gcttagtccc                         40

<210> SEQ ID NO 31
<211> LENGTH: 5
<212> TYPE: PRT
<213> ORGANISM: Homo sapiens

<400> SEQUENCE: 31

Gly Arg Phe Glu Arg
1               5

<210> SEQ ID NO 32
<211> LENGTH: 6
<212> TYPE: PRT
<213> ORGANISM: Homo sapiens

<400> SEQUENCE: 32

Pro Gly Arg Phe Glu Arg
1               5

<210> SEQ ID NO 33
<211> LENGTH: 7
<212> TYPE: PRT
<213> ORGANISM: Homo sapiens

<400> SEQUENCE: 33

Ser Pro Gly Arg Phe Glu Arg
1               5

<210> SEQ ID NO 34
<211> LENGTH: 10
<212> TYPE: PRT
<213> ORGANISM: Homo sapiens
```

```
<400> SEQUENCE: 34

Gly Arg Phe Glu Arg Ile Leu Leu Arg Ala
1               5                   10

<210> SEQ ID NO 35
<211> LENGTH: 10
<212> TYPE: PRT
<213> ORGANISM: Homo sapiens

<400> SEQUENCE: 35

Pro Gly Arg Phe Glu Arg Ile Leu Leu Arg
1               5                   10

<210> SEQ ID NO 36
<211> LENGTH: 11
<212> TYPE: PRT
<213> ORGANISM: Homo sapiens

<400> SEQUENCE: 36

Ser Pro Gly Arg Phe Glu Arg Ile Leu Leu Arg
1               5                   10

<210> SEQ ID NO 37
<211> LENGTH: 12
<212> TYPE: PRT
<213> ORGANISM: Homo sapiens

<400> SEQUENCE: 37

Ser Pro Gly Arg Phe Glu Arg Ile Leu Leu Arg Ala
1               5                   10

<210> SEQ ID NO 38
<211> LENGTH: 32
<212> TYPE: PRT
<213> ORGANISM: Homo sapiens

<400> SEQUENCE: 38

Gly Arg Phe Glu Arg Ile Leu Leu Arg Ala Ala Asn Thr His Ser Ser
1               5                   10                  15

Ala Lys Pro Cys Gly Gln Gln Ser Ile His Leu Gly Gly Val Phe Glu
            20                  25                  30

<210> SEQ ID NO 39
<211> LENGTH: 34
<212> TYPE: PRT
<213> ORGANISM: Homo sapiens

<400> SEQUENCE: 39

Gly Arg Phe Glu Arg Ile Leu Leu Arg Ala Ala Asn Thr His Ser Ser
1               5                   10                  15

Ala Lys Pro Cys Gly Gln Gln Ser Ile His Leu Gly Gly Val Phe Glu
            20                  25                  30

Leu Gln

<210> SEQ ID NO 40
<211> LENGTH: 42
<212> TYPE: PRT
<213> ORGANISM: Homo sapiens
```

<400> SEQUENCE: 40

Gly Arg Phe Glu Arg Ile Leu Leu Arg Ala Ala Asn Thr His Ser Ser
1               5                   10                  15

Ala Lys Pro Cys Gly Gln Gln Ser Ile His Leu Gly Gly Val Phe Glu
            20                  25                  30

Leu Gln Pro Gly Ala Ser Val Phe Val Asn
        35                  40

<210> SEQ ID NO 41
<211> LENGTH: 44
<212> TYPE: PRT
<213> ORGANISM: Homo sapiens

<400> SEQUENCE: 41

Ser Pro Gly Arg Phe Glu Arg Ile Leu Leu Arg Ala Ala Asn Thr His
1               5                   10                  15

Ser Ser Ala Lys Pro Cys Gly Gln Gln Ser Ile His Leu Gly Gly Val
            20                  25                  30

Phe Glu Leu Gln Pro Gly Ala Ser Val Phe Val Asn
        35                  40

<210> SEQ ID NO 42
<211> LENGTH: 39
<212> TYPE: DNA
<213> ORGANISM: Artificial Sequence
<220> FEATURE:
<223> OTHER INFORMATION: human IgG4 heavy-chain specific forward primer

<400> SEQUENCE: 42
gttaccgtct catctgcttc caccaagggc ccctccgtg                         39

<210> SEQ ID NO 43
<211> LENGTH: 39
<212> TYPE: DNA
<213> ORGANISM: Artificial Sequence
<220> FEATURE:
<223> OTHER INFORMATION: human IgG4 heavy-chain specific reverse primer

<400> SEQUENCE: 43
gaattctcat tgcccaggc tcagggacag ggacttctg                          39

<210> SEQ ID NO 44
<211> LENGTH: 39
<212> TYPE: DNA
<213> ORGANISM: Artificial Sequence
<220> FEATURE:
<223> OTHER INFORMATION: human kappa light-chain specific forward primer

<400> SEQUENCE: 44
ctggaaatta aacggactgt ggcggcacca tccgttttt                         39

<210> SEQ ID NO 45
<211> LENGTH: 39
<212> TYPE: DNA
<213> ORGANISM: Artificial Sequence
<220> FEATURE:
<223> OTHER INFORMATION: human kappa light-chain specific reverse primer

<400> SEQUENCE: 45
gaattctcaa cattcgcccc tgttaaagct ttttgtgac                         39

```
<210> SEQ ID NO 46
<211> LENGTH: 39
<212> TYPE: DNA
<213> ORGANISM: Artificial Sequence
<220> FEATURE:
<223> OTHER INFORMATION: human IgG4 constant 115 region CH reverse
      primer

<400> SEQUENCE: 46
caggaacacg gaaggtccgc cttcaaattc aggggcagg                              39

<210> SEQ ID NO 47
<211> LENGTH: 39
<212> TYPE: DNA
<213> ORGANISM: Artificial Sequence
<220> FEATURE:
<223> OTHER INFORMATION: human IgG4 constant 115 region CH forward
      primer

<400> SEQUENCE: 47
ccctgccctg cccctgaatt tgaaggcgga ccttccgtg                              39
```

CD40L BINDING POLYPEPTIDE

BACKGROUND OF THE INVENTION

Field

The present disclosure relates to a polypeptide that binds specifically to CD154, a pharmaceutical composition containing the same, and a method of treating diseases using the same.

Description of Related Technology

Cell-mediated immune responses and humoral immune responses are generated through the interaction of activated T cells with antigen-presenting cells. T-cell activation is not only dependent on the interaction of the antigen-specific T-cell receptor (TCR) with its cognate peptide-MHC complex, but also requires the coordinated binding and activation by a number of cell adhesion molecules and costimulatory molecules.

CD154 is one of such costimulatory molecules, and costimulatory signaling via such CD154 is necessary for T cell activation. In addition, signaling via CD40 to which CD154 binds is also required for antibody production after B cell activation. Thus, inhibition of CD154-CD40 interactions can inhibit both T-cell activation and antibody production, thus inhibiting both cell-mediated immune responses and humoral immune responses. In particular, during B cell activation and antibody production, anti-CD154 antibodies can inhibit responses in the following three stages (J. Clin. Invest. 2003; 112:1480-2): B cell help by activated T cells; germinal center generation; and T cell-B cell interaction in the germinal center.

Furthermore, the reported effects of anti-CD154 antibody, which inhibits the CD154-CD40 interaction, against diseases, include the treatment and prevention of autoimmune diseases including systemic lupus erythematosus (Boumpas et al. Arthritis Rheum. 2003; 48:719-727, Kelsoe G. J. Clin. Invest. 2003; 112:1480-1482), immune thrombocytopenic purpura (Kuwana et al. Blood 2004; 103:1229-1236), rheumatoid arthritis (Dune et al. Science 1993; 261:1328-1330), multiple sclerosis (Nagelkerken et al. J. Immunol. 2004; 173:993-999), and the inhibition of graft rejection in kidney (Kirk et al. Nat. Med. 1999; 5:686-689, Schuler et al. Transplantation 2004; 77:717-726), skin, heart and islet transplant recipients (Kirk et al. Philos. Trans. R Soc. Lond. B Biol. Sci. 2001; 356:691-702). This antibody was also able to inhibit graft-versus-host responses (Seung et al. Blood 2000; 95:2175). Particularly, systemic lupus erythematosus (Boumpas et al. Arthritis Rheum. 2003; 48:719-727, Kelsoe G. J. Clin. Invest. 2003; 112:1480-1482) and immune thrombocytopenic purpura (Kuwana et al. Blood 2004; 103:1229-1236) are representative antibody-mediated autoimmune diseases, and the therapeutic effects of anti-CD154 antibody against these autoimmune diseases in patients were proven. In addition, the graft rejection inhibitory effect of the anti-CD154 antibody in Rhesus and Cynomolgus monkey kidney transplant recipients was proven (Kirk et al. Nat. Med. 1999; 5:686-689, Schuler et al. Transplantation 2004; 77:717-726). Thus, anti-CD154 antibodies based on this finding have been developed. US Patent Publication No. 2004-0038293 discloses antibodies to human CD154.

However, it is a reality that the developed antibodies are not used in clinical practice due to the side effect of thrombus formation caused by platelet activation. In other words, the Fc portion of the previously developed antibodies has a problem in that it activates platelets by binding to the Fcγ receptor (FcγR) in platelets, resulting in thrombus formation.

Accordingly, there is a need to develop a substance that is capable of effectively inhibiting the CD154-CD40 interaction without the side effect of activating platelets.

SUMMARY OF THE INVENTION

The present disclosure has been made in order to solve the above-described problems, and is intended to provide a novel CD154 binding protein that has a reduced affinity for Fcγ receptor so as not to cause the side effects such as platelet activation and thrombus formation.

In one aspect, the present disclosure provides a CD154 binding polypeptide comprising: an HCDR1 amino acid sequence of SEQ ID NO:1, an HCDR2 amino acid sequence of SEQ ID NO:2 and an HCDR3 amino acid sequence of SEQ ID NO:3, which are from the heavy-chain complementarity determining region (HCDR) sequences of an immunoglobulin heavy-chain variable region (VH); and an LCDR1 amino acid sequence of SEQ ID NO:4, an LCDR2 amino acid sequence of SEQ ID NO:5 and an LCDR3 amino acid sequence of SEQ ID NO:6, which are from the light-chain complementarity determining region (LCDR) sequences of an immunoglobulin light-chain variable region (VL).

The polypeptide disclosed herein may specifically recognize CD154 protein, and may effectively inhibit the interaction of CD154 with CD40.

In one embodiment, the polypeptide disclosed herein specifically recognizes the amino acid sequence of CD154, represented by SEQ ID NO:12 or 13.

In this regard, the CD154 binding polypeptide according to the present disclosure is an anti-CD154 antibody or an antigen binding fragment thereof.

In one embodiment, the anti-CD154 antibody according to the present disclosure comprises a heavy-chain variable region having an amino acid sequence represented by SEQ ID NO:7 and a light-chain variable region having an amino acid sequence represented by SEQ ID NO:8. In one embodiment, in addition to these variable regions, the antibody according to the present disclosure comprises a heavy-chain constant region of SEQ ID NO:9 or 10 and a light-chain constant region of SEQ ID NO:11.

In one embodiment, the present disclosure also provides a polynucleotide encoding the polypeptide according to the present disclosure, which specifically recognizes CD154, and a vector comprising the polynucleotide.

The anti-CD154 antibody disclosed herein may be provided in various forms, and includes, for example, a monoclonal antibody, a chimeric antibody, a humanized antibody or a human antibody.

In one embodiment, the anti-CD154 antibody according to the present disclosure is a chimeric antibody, wherein the chimeric antibody comprises a variable region of non-human origin and an Fc region of human origin, wherein the Fc region of human origin is selected from IgG1 Fc, IgG2 Fc, IgG3 Fc and IgG4 Fc. In addition, the chimeric antibody has a reduced binding affinity for Fcγ receptor (FcγR), and thus platelet activation by the chimeric antibody is reduced.

In one embodiment, the Fc region included in the chimeric antibody according to the present disclosure is IgG4 Fc, wherein the IgG4 Fc comprises an amino acid substitution mutation, wherein the mutation is a leucine-to-glutamic acid substitution (L115E) at amino acid residue 115 of SEQ ID NO:9. The binding affinity of the chimeric antibody for Fcγ receptor (FcγR) is reduced by the substitution, and for this reason, platelet activation by the chimeric antibody is reduced.

The antibody according to the present disclosure may be provided as a conjugate with a substance selected from the group consisting of therapeutic agents, prodrugs, peptides, proteins, enzymes, viruses, lipids, biological modifiers, drugs and PEG, depending on the specific purpose thereof.

The antibody according to the present disclosure is capable of effectively blocking the CD154-CD40 interaction to inhibit both T cell activation and antibody production, thus inhibiting both cell-mediated immune responses and humoral immune responses. Accordingly, the polypeptide according to the present disclosure, which specifically recognizes CD154 to inhibit the CD154-CD40 interaction, may be effectively used for the treatment, prevention or control of antibody-mediated symptoms or diseases.

Therefore, in one aspect, the present disclosure provides a pharmaceutical composition for treating or preventing T cell-mediated or antibody-mediated immune diseases or symptoms.

In another aspect, the present disclosure provides a composition for inhibiting anti-drug antibody production, which comprises the CD154 binding polypeptide according to the present disclosure. The composition may be effectively used to inhibit antibody production caused by administration of antibody-based drugs, for example, Enbrel, Humira or the like.

In the pharmaceutical composition for treating or preventing T cell-mediated or antibody-mediated immune diseases or symptoms, the T cell-mediated or antibody-mediated immune diseases or symptoms represent anti-drug antibody, autoimmune diseases, including systemic lupus erythematosus, immune thrombocytopenic purpura, rheumatoid arthritis and multiple sclerosis, and rejection against transplantation of organs or tissues, including islet, kidney, heart and skin, or graft-versus-host diseases.

In another aspect, the present disclosure provides an anti-CD154 antibody or an antigen-binding fragment thereof, which recognizes an epitope comprising a CD40 ligand portion consisting of 5 to 50 amino acids, including Gly at residue 199, Arg at residue 200 and Arg at residue 203 in a CD40 ligand represented by SEQ ID NO:22, which is a CD40-interacting region of CD154 protein, in which the anti-CD154 antibody or the antigen-binding fragment also interferes with the CD154-CD40 interaction.

The epitope may be a polypeptide consisting of 5 to 50 amino acids, which further comprises one or more of Glu at residues 207 and 230, and Gln at residue 232.

The epitope according to the present disclosure can be easily determined by a person skilled in the art with reference to the above-described conditions, and may be present between residue 191 and residue 240. In one embodiment, the epitope comprises GRFER (SEQ ID NO:31), PGRFER (SEQ ID NO:32), SPGRFER (SEQ ID NO:33), GRFERILLRA (SEQ ID NO:34), PGRFERILLR (SEQ ID NO:35), SPGRFERILLR (SEQ ID NO:36), SPGRFERILLRA (SEQ ID NO:37), GRFERILLRAANTHSSAKPCGQQSIHLGGVFE (SEQ ID NO:38), GRFERILLRAANTHSSAKPCGQQSIHLGGVFELQ (SEQ ID NO:39), GRFERILLRAANTHSSAKPCGQQSIHLGGVFELQPGASVFVN (SEQ ID NO:40), or SPGRFERILLRAANTHSSAKPCGQQSIHLGGVFELQPGASVFVN (SEQ ID NO:41), which is present between residue 197 and residue 240, particularly between residue 197 and residue 232, but the scope of the present disclosure is not limited thereto as long as the above-described conditions are satisfied.

The polypeptide according to the present disclosure, which specifically recognizes CD154, specifically recognizes a portion of CD154, which interacts with CD40, and thus it interferes with the CD154-CD40 interaction. In this regard, the present disclosure also provides an anti-CD154 antibody or an antigen-binding fragment thereof, which specifically recognizes a second hydrophilic contact region and/or a charge interaction region, which is the CD40-interacting regions of CD154 protein.

As described above, the polypeptide according to the present disclosure, which specifically recognizes CD154, can inhibit both T cell activation and antibody production, and thus inhibit both cell-mediated immune responses and humoral immune responses.

In this regard, the present disclosure provides the kit comprising the polypeptide, antibody or its antigen-binding fragment, or chimeric antibody according to the present disclosure, which specifically recognizes CD154, for inhibiting either anti-drug antibody production or CD154-dependent T cell-mediated immune responses.

The present disclosure also provides the use of the CD154 binding polypeptide, antibody or its antigen binding fragment, or chimeric antibody according to the present disclosure.

The present disclosure also provides the use of the CD154 binding polypeptide, antibody or antigen binding fragment thereof, or chimeric antibody according to the present disclosure, for inhibition of anti-drug antibody production, inhibition of antibody-mediated immune responses, inhibition of CD154-dependent T cell-mediated immune responses, or prevention or treatment of diseases related thereto as described above.

The present disclosure also provides a method for inhibition of anti-drug antibody production, a method for inhibition of antibody-mediated immune responses, or a method for inhibition of CD154-dependent T cell-mediated immune responses, the method comprising a step of treating cells with the CD154 binding polypeptide, antibody or its antigen binding fragment, or chimeric antibody according to the present disclosure, wherein the method may be performed in vitro, in vivo or ex vivo.

The present disclosure also provides a method for inhibition of anti-drug antibody production, a method for inhibition of antibody-mediated immune responses, a method for inhibition of CD154-dependent T cell-mediated immune responses, or a method for prevention or treatment of diseases related thereto as described above, the method comprising a step of administering a therapeutically effective amount of the CD154 binding polypeptide, antibody or its antigen binding fragment, or chimeric antibody according to the present disclosure.

The antibody according to the present disclosure, which specifically recognizes CD154, can effectively inhibit the CD154-CD40 interaction without activating platelets, and thus can be effectively used for the prevention or treatment of various diseases or symptoms, which requires inhibition of the interaction. For example, the antibody according to the present disclosure can effectively inhibit anti-drug antibody formation, can also be effectively used for treatment of autoimmune diseases, including systemic lupus erythematosus, immune thrombocytopenic purpura, rheumatoid arthritis or multiple sclerosis, and enables allogeneic and xenogeneic organ transplantation, cell transplantation, bone marrow transplantation or stem cell transplantation without immune rejection so as to eliminate the need to use immunosuppressants or to minimize the kind and amount of immunosuppressants used in combination therapy.

BRIEF DESCRIPTION OF THE DRAWINGS

FIG. 1 shows the results of flow cytometry performed to analyze the binding of an anti-human CD154 antibody according to one embodiment of the present disclosure to an antigen.

FIG. 2 shows the results of western blotting to detect an antigen epitope which is recognized by the present anti-CD154 antibody.

FIG. 3 shows the results of analyzing the inhibitory effects of human IgG4 and IgG4 (L115E) anti-human CD154 chimeric antibodies according to one embodiment of the present disclosure against the CD154-CD40 interaction.

FIG. 4 is a restriction map of a vector used in the production of a human IgG4 chimeric anti-CD154 antibody according to one embodiment of the present disclosure.

FIG. 5 shows the results of flow cytometry performed to analyze the binding of human IgG4 and IgG4 (L115E) anti-human CD154 chimeric antibodies according to one embodiment of the present disclosure to an antigen.

FIG. 6 shows the results of analyzing the inhibitory effects of an IgG4 (L115E) anti-human CD154 chimeric antibody according to one embodiment of the present disclosure against T cell-dependent immune responses, and indicates that the present antibody can effectively inhibit the formation of an anti-drug antibody to Humira.

FIG. 7 shows the results of analyzing the effects of human IgG4 and IgG4 (L115E) anti-human CD154 chimeric antibodies according to one embodiment of the present disclosure on platelet activation in CD32a transgenic mice, and indicates that the present IgG4 chimeric antibody reduced the number of platelets, but the IgG4 (L115E) chimeric antibody did not reduce the number of platelets compared to a normal control group.

DETAILED DESCRIPTION OF THE EMBODIMENTS

The present disclosure relates to a polypeptide that specifically recognizes CD154 molecules.

In one embodiment, the present disclosure is directed to a CD154 binding polypeptide comprising: an HCDR1 amino acid sequence of SEQ ID NO:1, an HCDR2 amino acid sequence of SEQ ID NO:2 and an HCDR3 amino acid sequence of SEQ ID NO:3, which are the heavy-chain complementarity determining region (HCDR) sequences of an immunoglobulin heavy-chain variable region (VH); and amino acid sequences of an LCDR1 amino acid sequence of SEQ ID NO:4, an LCDR2 amino acid sequence of SEQ ID NO:5 and an LCDR3 amino acid sequence of SEQ ID NO:6, which are the light-chain complementarity determining region (LCDR) sequences of an immunoglobulin light-chain variable region (VL).

A CD154 molecule which is specifically recognized by the polypeptide according to the present disclosure is an about 32-39 kDa protein, called CD40 ligand, CD40L or gp39, which is primarily expressed in activated T cells. It is a member of the TNF molecular family, which is known to also be expressed in platelets and other types of cells, including mast cells, macrophages, basophils, natural killer cells, B lymphocytes, and non-haematopoietic cells (e.g., smooth muscle cells, epithelial cells, and endothelial cells). It is a type II transmembrane protein composed of a cytoplasmic region, a transmembrane region and an extracellular region, located sequentially from the N-terminus, but is also found as 14, 18, and 29 kDa soluble molecules. It exhibits its effect by binding to CD40 expressed in antigen-presenting cells (APCs), and is a costimulatory molecule which induces T cell activation together with T cell receptor stimulation by MHC molecules and is also involved in APC activation.

CD154 which is recognized by the polypeptide of the present disclosure is of mammalian origin. Particularly, the polypeptide of the present disclosure recognizes CD154 of human origin or non-human primate origin, for example, Rhesus, Cynomolgus or chimpanzee origin. The gene and protein sequences of CD154 are known, and for example, are known as GenBank Accession Nos. NM-000074.2 and NP-000065.1 for humans. In one embodiment, the polypeptide of the present disclosure specifically recognizes CD154 of human or non-human primate origin.

The polypeptide of the present disclosure can recognize full-length CD154 and its fragments, for example, soluble CD154.

The polypeptide according to the present disclosure specifically recognizes CD154. Particularly, it specifically recognizes a portion of CD154, which interacts with CD40. More particularly, it specifically recognizes a CD40 ligand (e.g., SEQ ID NO:22). Residues in the CD40 ligand, which interact with CD40, were previously identified by 3D crystal structure analysis, and for these residues, reference may be made to An et al (J. Biol. Chem. 2011; 286:11226-11235).

Therefore, in this regard t, the polypeptide according to the present disclosure provides an anti-CD154 antibody or an antigen-binding fragment thereof, which recognizes an epitope comprising a CD40 ligand portion consisting of 5 to 50 amino acids, including Gly at residue 199, Arg at residue 200 and Arg at residue 203 in a CD40 ligand represented by SEQ ID NO:22, which is a CD40-interacting region of CD154 protein, in which the anti-CD154 antibody or the antigen-binding fragment also interferes with the CD154-CD40 interaction. The epitope may be a polypeptide consisting of 5 to 50 amino acids, which further comprises one or more of Glu at residues 207 and 230 and Gin at residue 232.

The epitope according to the present disclosure can be easily determined by a person skilled in the art with reference to the above-described conditions, and may be present between residue 191 and residue 240 in the sequence of SEQ ID NO:22. In one embodiment, the epitope comprises GRFER (SEQ ID NO:31), PGRFER (SEQ ID NO:32), SPGRFER (SEQ ID NO:33), GRFERILLRA (SEQ ID NO:34), PGRFERILLR (SEQ ID NO:35), SPGRFERILLR (SEQ ID NO:36), SPGRFERILLRA (SEQ ID NO:37), GRFERILLRAANTHSSAKPCGQQSIHLGGVFE (SEQ ID NO:38), GRFERILLRAANTHSSAK-PCGQQSIHLGGVFELQ (SEQ ID NO:39), GRFER-ILLRAANTHSSAKPCGQQSIHLGGVFELQPGASVFVN (SEQ ID NO:40), or SPGRFERILLRAANTHSSAK-PCGQQSIHLGGVFELQPGASVFVN (SEQ ID NO:41), which is present between residue 197 and residue 240, particularly between residue 197 and residue 232, but the scope of the present disclosure is not limited thereto as long as the above-described conditions are satisfied.

The polypeptide according to the present disclosure, which specifically recognizes CD154 as described above, specifically recognizes the CD40-interacting portion of CD154, particularly a second hydrophilic contact region and a charge interaction region (An et al. J. Bio. Chem. 2011; 286:11226-11235), and interferes with the CD154-CD40 interaction. According to the literature, CD154 comprises three contact regions that interact with CD40, including a hydrophobic contact region, a first hydrophilic contact region and a second hydrophilic contact region comprising G199, 8200, 8203 and Q232 residues of SEQ ID NO:22, and a charge interaction region (comprising 8200, 8203, 8207 and E230). The polypeptide according to the present disclosure, to which specifically recognizes CD154, specifically recognizes the second contact region and/or the charge interaction region.

In this regard, the present disclosure also provides an anti-CD154 antibody or an antigen binding fragment thereof, which specifically recognizes a second hydrophilic contact region and/or a charge interaction region, which is the CD40-interacting region of CD154 protein.

An epitope which is recognized by the polypeptide according to the present disclosure, which specifically recognizes CD154, consists of about 5 to 71 amino acids, including the above-described residues, and for an example thereof, reference may be made to the above description.

In one embodiment, the CD154 binding polypeptide according to the present disclosure may be provided in various forms as long as it has the features described herein. Particularly, the CD154 binding polypeptide may be provided as an anti-CD154 antibody or an antigen binding fragment thereof.

As used herein, the term "antibody" refers to proteins that bind to other molecules (antigens) through their light-chain and heavy-chain variable regions, and include IgG, IgD, IgA and IgE types. The antibodies include polyclonal antibodies, monoclonal antibodies and multispecific antibodies. In addition, the antibodies of the present disclosure include monoclonal antibodies having various types of structures, for example, intact antibodies (Abs) comprising two full-length heavy chains and two full-length light chains, as well as their fragments comprising or not comprising a constant region, chimeric antibodies, human antibodies, humanized antibodies, or other genetically engineered antibodies having the features described herein.

As used herein, the term "antigen binding fragment" refers to a portion of the above-described intact antibody, one or more sequences of which are shorter in length than the amino acid sequence of the intact antibody. In functional respects, the antigen binding fragment comprises the activity or function of at least a portion of the intact antibody or the parent antibody, and examples thereof include, but are not limited to, Fab (fragment for antigen binding), Fab', F(ab')$_2$, Fv or single chain antibody (SCA) (e.g., scFv or dsFv), bispecific scFv and diabody.

As used herein, the term "variable region" refers to an antigen binding region formed by a portion of each of a heavy chain and a light chain. Each variable region comprises 4 framework regions (FRs) having conserved sequences and 3 complemental)/determining regions (CDRs) having severe sequence variations. The CDRs of an immunoglobulin heavy-chain variable region (VH) are referred to as HCDR1 to HCDR3, and the CDRs of an immunoglobulin light-chain variable region (VL) are referred to as LCDR1 to LCDR3.

As used herein, the term "complementarity determining region" refers to a region that determines the specificity and binding affinity of an antibody for an antigen. Sequence variation between antibodies is most frequently found in the complementary/determining regions. Among these complementary determining regions, the CDR3 region shows the most severe variation and consists of at least 2 to at most 26 amino acid residues. Regions other than CDRs in VH and VL are referred to as framework regions. The backbone of the antigen binding polypeptide according to the present disclosure may comprise, as a consensus sequence, a sequence found in naturally occurring human antibodies or a sequence found in various antibodies.

Any person skilled in the art will appreciate that an antibody comprising constituent elements, including variable regions, can be constructed using variable regions having the sequences of SEQ ID NOs: 1 to 6 as described above. In one embodiment of the present disclosure, the heavy-chain variable region of the antibody according to the present disclosure has an amino acid sequence of SEQ ID NO:7, and the light-chain variable region of the antibody has an amino acid sequence of SEQ ID NO: 8. In other embodiments, the heavy-chain constant region of the antibody according to the present disclosure is represented by an amino acid sequence of SEQ ID NO:9 or 10, and the light-chain constant region of the antibody is represented by an amino acid sequence of SEQ ID NO:11.

The present disclosure also includes those wherein conservative substitution at amino acid residues in SEQ ID NOs: 1 to 11 occurred. In one embodiment of the present disclosure, the sequences are those wherein conservative substitution at less than 10, less than 9, less than 8, less than 7, less than 6, less than 5, less than 4, less than 3, less than 2 or 1 amino acid residue occurred. As used herein, the term "conservative substitution" is a term widely used in the art, which indicates that one amino acid is substituted with another amino acid having similar characteristics. The similar characteristics include, for example, size, hydrophobicity, or charge. Amino acids are generally classified according to the electrical characteristics of their side chains into amino acids having positively charged side chains, negatively charged side chains, uncharged side chains or hydrophobic side chains. For example, conservative substitutions include leucine (Leu)-to-isoleucine (ile) substitution, arginine (Arg)-to-lysine (Lys) substitution, phenylalanine (Phe)-to-tryptophan (Trp) substitution, aspartic acid (Asp)-to-glutamic acid (Glu) substitution, or serine (Ser)-to-threonine (Thr) substitution, or vice versa. Generally, conservative substitution of the CDR sequences does not affect the function of the CDRs.

A method for such sequence substitution is known in art, and for this method, reference may be made to, for example, Sambrook, Molecular Cloning A Laboratory Manual (Fourth Edition), Cold Spring Harbor Laboratory (2012) N.Y.

The antibodies according to the present disclosure include antigen-binding fragments, variants or derivatives thereof, including, but not limited to, polyclonal, monoclonal, multispecific, human, humanized, primatized or chimeric antibodies, single chain antibodies, epitope-binding fragments, for example, Fab, Fab', F(ab')2, F(ab)$_2$, Fd, Fvs, single-chain Fvs (scFv), disulfide-linked Fvs (sdFv), and fragments comprising either a $V_L$ or $V_H$ domain. The antibodies according to the present disclosure may be of any type (e.g., IgG, IgE, IgM, IgD, IgA, or IgY), any class (e.g., IgG1, IgG2, IgG3, IgG4, IgA1, or IgA2), or subclass of immunoglobulin molecule.

The antibody or antibody fragment according to the present disclosure may be a chimeric antibody. As used herein, the term "chimeric antibody" means that at least a portion of a variable region (i.e., antigen-binding region) and at least a portion of an antibody constant region (comprising CL1 for a light chain and comprising CH1, CH2 and CH3 regions for a heavy chain) are of different species origins. For example, the variable region may be of mouse origin, and the constant region may be of human origin.

Alternatively, the term "chimeric antibody means class-switched antibodies, for example, antibodies obtained by IgG-to-IgE class switching. Chimeric antibodies are generally produced by recombinant DNA technology, and reference may be made to, for example, Morrison et al. Proc. Nat'l. Acad. Sci. USA 1984; 81:6851-6885, and the disclosure of U.S. Pat. No. 5,202,238.

In one embodiment of the present disclosure, the antibody of the present disclosure is a chimeric antibody. For example, the antibody of the present disclosure may be a human antibody having light-chain and heavy-chain variable regions derived from a mouse antibody produced herein, for example, an antibody produced by grafting mouse heavy-chain and kappa light-chain variable regions into a human IgG4 heavy-chain constant region and a human kappa light-chain constant region.

In one embodiment of the present disclosure, the chimeric antibody comprises an Fc region selected from human IgG1, IgG2, IgG3 and IgG4 Fc, particularly IgG4 Fc, more particularly an Fc region having a mutation introduced therein. The mutation includes one wherein the hydrophobic amino acid at residue 115 in the amino acid sequence represented by SEQ ID NO:9, which is the sequence of the heavy-chain constant region of an IgG4 antibody according to one embodiment of the present disclosure, is substituted with an acidic amino acid. Particularly, the mutation includes a leucine-to-glutamic acid substitution as shown in SEQ ID NO:10. The temp "Fc (fragment crystallizable)" refers to the CH2 and CH3 regions of the heavy chain. The chimeric antibody according to the present disclosure, particularly an antibody comprising human IgG4 Fc, had a reduced binding affinity for Fcγ receptor (FcγR), compared to an antibody whose Fc was not substituted, and thus platelet activation by the antibody was significantly reduced.

In one embodiment, the chimeric antibody according to the present disclosure comprises: a heavy chain comprising a heavy-chain variable region sequence (SEQ ID NO:7) and a heavy-chain constant region sequence (SEQ ID NO:9 or SEQ ID NO:10); and a light chain comprising a kappa light-chain variable region sequence (SEQ ID NO: 8) and a kappa light-chain constant region sequence (SEQ ID NO:11).

The antibody or antibody fragment according to the present disclosure may be a humanized antibody. As used herein, the term "humanized antibody" refers to an antibody which is composed of a human antibody framework and in which a portion of CDR regions has been modified to include only a portion of the CDRs of the species from which the antibody molecule was originally derived, in which the included portion is essential for specific binding to an antigen. For example, among CDRs of antibodies of monkey or mouse origin, the CDR portions other than a portion essential for specific binding to an antigent, and the light-chain and heavy-chain frameworks are replaced with a human antibody. For a method for producing the humanized antibody, reference may be made to, for example, Riechmann et al. Nature 1988; 332:323-327.

The antibody or antibody fragment according to the present disclosure may be a monoclonal antibody. The monoclonal antibody can be produced by various methods known in the art, which are based on the fusion of myeloma cells with immunized spleen cells of mammalian origin. In other embodiments, the antibody of the present disclosure includes an antibody fragment comprising: one or more CDRs derived from the light chain of an antibody produced in the above-described hybridoma; and/or one or more CDRs derived from the heavy chain of the antibody.

Furthermore, the antibodies, antigen binding fragments, variants or derivatives thereof according to the present disclosure may be conjugated with functional substances such as therapeutic agents, prodrugs, peptides, proteins, enzymes, viruses, lipids, biological response modulators or PEG (polyethylene glycol), for various purposes. These may be produced using various methods depending on the kind of substance that is conjugated therewith. For example, reference may be made to Amon et al. "Monoclonal Antibodies For Immunotargeting Of Drugs In Cancer Therapy", in Monoclonal Antibodies And Cancer Therapy, Reisfeld et al. (eds.), pp. 243-56 (Alan R Liss, Inc. (1985); Hellstrom et al. "Antibodies For Drug Delivery", in Controlled Drug Delivery (2nd Ed.), Robinson et al. (eds.), Marcel Dekker, Inc., pp. 623-53 (1987).

An antibody fragment can be obtained by treatment with pepsin or papain. A F(ab')2 fragment can be obtained by treating an intact antibody with pepsin, and subsequent treatment of the F(ab')$_2$ fragment with a thiol reducing agent can afford an Fab fragment comprising a portion of the light chain and a portion of the heavy chain. A Fab fragment can also be obtained by treating an intact antibody with papain. For example, an antibody fragment such as F(ab')$_2$ or Fab, which specifically recognizes CD154, can be produced by pepsin or papain treatment of the antibody produced in the hybridoma of the present disclosure.

A Fv fragment is an antibody fragment composed only of heavy-chain and light-chain variable regions, in which the two variable regions can be linked to each other by a chemical crosslinking agent or a non-covalent or covalent bond such as an intermolecular disulfide bond (Inbar et al. Proc. Nat'l. Acad. Sci. USA 1972; 69:2659-2662). For example, an antibody that specifically recognizes CD154 can be constructed either by isolating only heavy-chain and light-chain variable regions by enzymatic treatment of the antibody produced in the hybridoma of the present disclosure or by use of recombinant DNA technology.

An SCA fragment can be produced by enzymatic treatment or a genetic engineering technique, and is an antibody fragment wherein a light-chain variable region and a heavy-chain variable region are linked to each other by a linker such as a polypeptide. For a method for production of scFv, reference may be made to, for example, the disclosure of U.S. Pat. Nos. 4,936,778 or 5,892,019. An antibody that specifically recognizes CD154 can be constructed either by enzymatic treatment of the antibody produced in the hybridoma of the present disclosure or by recombinant DNA technology, for example, a technology comprising constructing a nucleic acid sequence encoding the heavy-chain and/or light-chain variable region of the antibody and expressing the vector in a suitable cell.

As used herein, the term "binding" or "specific binding" refers to the affinity of the antibody or antibody composition of the present disclosure for an antigen "Specific binding" in antigen-antibody binding can typically be distinguished from nonspecific background binding when the dissociation constant (Kd) is less than $1\times10^{-5}$M or less than $1\times10^{-6}$M or less than $1\times10^{-7}$M. Specific binding can be detected by a method known in the art, for example, ELISA, SPR (surface plasmon resonance), immunoprecipitation, coprecipitation or the like, which includes a suitable control enabling specific binding to be distinguished from nonspecific binding.

The antibodies of the present disclosure, including intact antibodies or fragments thereof as described above, may be present as multimers such as dimers, trimers, tetramers, pentamers or the like, which comprise at least a portion of monomeric antigen binding regions. Such multimers also include homomultimers or heteromultimers. Antibody multimers comprise a number of antigen binding regions, and thus have an excellent binding affinity for antigens, compared to monomers. Antibody multimers are also useful for construction of multifunctional (bifunctional, trifunctional or tetrafunctional) antibodies.

As used herein, the term "multifunctional" refers to an antibody or antibody composition having two or more activities or functions (e.g., antigen binding affinity, enzyme activity, ligand or receptor binding affinity, etc.). For example, the antibody of the present disclosure may be bound to a polypeptide having enzymatic activity, for example, luciferase, acetyltransferase, galactosidase or the like.

Multifunctional antibodies also include multivalent or multispecific (bispecific, trispecific, etc.) antibodies. The term "multispecific" includes a variable region capable of binding to two or more different epitopes. The two or more epitopes may be present in a single antigen or different antigens.

In another aspect, the present disclosure is also directed to a polynucleotide or nucleic acid molecule encoding the whole or a part of the polypeptide according to the present disclosure, a vector comprising the polynucleotide, or a transformant comprising the vector.

Nucleic acids include, for example, DNA, cDNA, RNA, or recombinant or synthetic DNA or RNA. In one embodiment, the nucleic acid molecule is cDNA. The nucleic acid may also be a corresponding genomic DNA or a fragment thereof. The nucleic acid sequence encoding the antibody according to the present disclosure or a portion thereof or a fragment thereof may be different due to the redundancy of the nucleic acid sequence encoding the amino acid sequence, and this sequence is also included in the scope of the present disclosure. In one embodiment of the present disclosure, the polynucleotide sequences of HCDR1, HCDR2 and HCDR3 of the heavy chain of the antibody according to the present disclosure are represented by SEQ ID NOs: 14, 15 and 16, respectively, and a polynucleotide sequence encoding the heavy-chain variable region of the antibody is represented by SEQ ID NO:17. In addition, the polynucleotide sequences of LCDR1, LCDR2 and LCDR3 of the light chain of the antibody according to the present disclosure are represented by SEQ ID NOs: 18, 19 and 20, and a polynucleotide sequence encoding the light-chain variable region of the antibody is represented by SEQ ID NO:21.

In another aspect, the present disclosure is also directed to a vector comprising the nucleic acid molecule, which can express the nucleic acid molecule. Vectors that may be used in the present disclosure include, for example, phages, plasmids, replicable or non-replicable viral or retroviral vectors. The nucleic acid molecule according to the present disclosure may be introduced into a variety of known vectors. For example, the vectors include, but are not limited to, vectors for prokaryotic cells, including pUC-based vectors, pBluescript (Stratagene, La Jolla, Calif., USA), pET-based vectors (Novagen, Madison, Wis., USA) or pCR®TOPO (Invitrogen, Gaithersburg, Md., USA) vectors, and vectors for eukaryotic cells, including pREP (Invitrogen), pcDNA3 (Invitrogen), pCEP4 (Invitrogen), pMCI neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech, Palo, Alto, Calif., USA), pIRES-EGFP (Clontech), pEAK-10 (Edge Biosystems), pTriEx™-Hygro (Novagen) vectors and pCI-Neo (Promega, Madison, Wis., USA) vectors.

The vector according to the present disclosure may be introduced into a variety of known prokaryotic cells or eukaryotic cells by known transformation or transfection techniques. For intracellular introduction, the vector may be inserted into the genome of host cells or may be present as an extra chromosome.

Prokaryotic cells that may be used in the present disclosure include cells belonging to the species *Escherichia*, *Bacillus*, *Streptomyces* and *Salmonella*, and eukaryotic cells that may be used in the present disclosure include, but are not limited to, for example, mammalian cells, for example, Hela, HEK293, H9, Jurkat, mouse NIH3T3, C127, Cos1, Cos7 and CV1, mouse C2C12, BHI or CHO cells; fungal cells such as *Saccharomyces cerevisiae* or *Pichia pastoris*, and insect cells such as *Drosophila* S2 and *Spodoptera* Sf9.

The antibody of the present disclosure may be produced according to a known method using a recombinant technique. In a recombinant technique, the antibody of the present disclosure can be obtained by cloning a nucleic acid sequence encoding the heavy chain of the antibody and a sequence encoding the light chain of the antibody into one or two expression vectors, introducing the vector into eukaryotic host cells to express the antibody, and then isolating the antibody from the host cells or the medium. This recombinant technique comprising construction of a vector, expression of a protein from the constructed vector in cells, and isolation of the protein, is known in the art, and for this technique, reference may be made to, for example, the disclosure of Kaufman R. J. Mol. Biotechnol. 2000; 16:151-160. The vector encoding the antibody of the present disclosure can be expressed in suitable host cells, for example, CHO cells, NS0 cells, SP2/0 cells, HEK293 cells, COS cells, or yeast or E coil cells, and the antibody may be collected from a lysate of the cells or the culture medium.

The nucleic acid sequence encoding the whole of the antibody of the present disclosure or a fragment thereof may be isolated from the hybridoma cells disclosed herein according to a conventional method, and then sequenced. Then, the isolated nucleic acid sequence may be cloned into a suitable expression vector as described above, and then introduced into HEK293 cells, CHO cells or NS0 cells, which produced no antibody, and a recombinant antibody can be produced in the host cells. The nucleic acid encoding the antibody of the present disclosure or a fragment thereof is introduced into an expression vector comprising a promoter, a translation initiation region, a 3' untranslated region, a polyadenylation signal and a transcription termination signal. The light chain and the heavy chain may be introduced into a single vector or separate vectors.

For expression of the antibody in NS0 cells, reference may be made to, for example, the disclosure of Barnes et al. Cytotechnology 2000; 32:109-123, Norderhaug et al. J. Immunol. Methods 1997; 204:77-87, and the like. For expression of the antibody in HEK cells, reference may be made to the disclosure of Schlaeger E. J. J. Immunol. Methods 1996; 194:191-199, and the like.

The antibody of the present disclosure may be present in intact cells including the hybridoma, a lysate of the cells or a culture medium, and may be purified and isolated therefrom in a partially or substantially pure form. Purification of the antibody may be performed using known techniques such as alkaline/SDS treatment, CsCl banding, column chromatography, agarose gel electrophoresis in order to remove other cellular byproducts other than the antibody, for example, cellular components, nucleic acids, proteins and the like. For purification of the antibody, reference may be made to, for example, the latest edition of Ausubel et al., Current Protocols in Molecular Biology, Greene Publishing and Wiley Interscience, New York.

A monoclonal antibody can be isolated from the medium used for culture of the hybridoma cells disclosed herein, by use of a conventional method such as Protein A-Sepharose, hydroxyapatite chromatography, dialysis, or affinity chromatography, after culture of the hybridoma cells.

In still another aspect, the present disclosure is directed to a pharmaceutical composition containing, as an active ingredient, the polypeptide disclosed herein, which is formulated with a pharmaceutically acceptable carrier and optionally an excipient or a stabilizer.

As used herein, the term "pharmaceutically acceptable carrier" includes physiologically acceptable substances, for example, any solvents, dispersing media, coating agents, antibacterial and antifungal agents, isotonic solutions, absorption/resorption retardants, and the like. In one embodiment, the carrier used is particularly a substance suitable for injection and infusion. For example, the pharmaceutically acceptable carrier may include a sterile aqueous solution, an isotonic buffered saline, or sterile powder for preparation of a dispersion or a sterile injectable solution. Any person skilled in the art may select a suitable formulation depending on the kind of active ingredient that is contained in the composition.

It is obvious to a person skilled in the art that the composition of the present disclosure may be administered by various routes known in the art and that the mode and route of administration may vary depending on a desired effect. The antibody or fragment thereof according to the present disclosure, or a composition comprising the same, may be administered parenterally, for example, by intravenous injection, bolus injection, or intramuscular or subcutaneous injection. In addition, the composition of the present disclosure may be administered as a pharmaceutically acceptable dosage form, for example, a hydrated form such as an aqueous solution, or a freeze-dried form, regardless of the route of administration.

The polypeptide disclosed herein, which specifically recognizes CD154, effectively inhibits the interaction of CD154 with CD40. The blocking of the CD154-CD40 interaction can inhibit both T cell activation and antibody production, thus inhibiting both cell-mediated immune responses and humoral immune responses. For T cell activation, costimulatoiy signaling through CD154 is necessarily required, and, for B cell activation, signaling through CD40 is required.

Particularly, during B cell activation and antibody production, anti-CD154 antibodies can inhibit responses in the following three stages (J. Clin. Invest. 2003; 112:1480-1482): B cell help by activated T cells; germinal center generation; and T cell-B cell interaction in the germinal center.

Furthermore, the reported effects of anti-CD154 antibody, which inhibits the CD154-CD40 interaction, against diseases, include the treatment and prevention of autoimmune diseases including systemic lupus erythematosus (Boumpas et al. Arthritis Rheum. 2003; 48:719-727, Kelsoe G. J. Clin. Invest. 2003; 112:1480-1482), immune thrombocytopenic purpura (Kuwana et al. Blood 2004; 103:1229-1236), rheumatoid arthritis (Dune et al. Science 1993; 261:1328-1330), multiple sclerosis (Nagelkerken et al. J. Immunol. 2004; 173:993-999), and the inhibition of graft rejection such as in kidney (Kirk et al. Nat. Med. 1999; 5:686-689, Schuler et al. Transplantation 2004; 77:717-726), skin, heart and islet transplant recipients (Kirk et al. Philos. Trans. R Soc. Lond. B Biol. Sci. 2001; 356:691-702) and graft-versus-host responses (Seung et al. Blood 2000; 95:2175). Particularly, systemic lupus erythematosus (Boumpas et al. Arthritis Rheum. 2003; 48:719-727, Kelsoe G. J. Clin. Invest. 2003; 112:1480-1482) and immune thrombocytopenic purpura (Kuwana et al. Blood 2004; 103:1229-1236) are representative antibody-mediated autoimmune diseases, and the therapeutic effects of anti-CD154 antibody against these autoimmune diseases in patients were proven. In addition, the graft rejection inhibitory effect of the anti-CD154 antibody in kidney transplant recipients of Rhesus and Cynomolgus monkeys was proven (Kirk et al. Nat. Med. 1999; 5:686-689, Schuler et al. Transplantation 2004; 77:717-726). Furthermore, it was proven that the anti-CD154 antibody according to the present disclosure can also inhibit the production of an anti-drug antibody to Humira.

Accordingly, the antibody according to the present disclosure can effectively inhibit the CD154-CD40 interaction to inhibit both T cell activation and antibody production, and thus can be effectively used to inhibit the above-described anti-drug antibody production, autoimmune diseases, graft rejection and graft-versus-host diseases.

Furthermore, unlike conventional antibodies that could not be applied in the clinical practice due to their side effects of thrombus formation caused by platelet activation, the polypeptide or anti-CD154 antibody according to the present disclosure, which specifically recognizes CD154, has a reduced affinity for FcγR as a result of substituting certain residues in the Fc portion, and thus has an advantage in that it does not cause the side effect of platelet activation and thrombus formation. Thus, the polypeptide of the present disclosure is very advantageous for clinical applications.

Accordingly, the polypeptide antibody or antigen binding fragment described herein, or a pharmaceutical composition containing the same, may be effectively used for the treatment or prevention of T cell-mediated or antibody-mediated immune diseases.

In this regard, the phrase "T cell-mediated or antibody-mediated immune diseases or symptoms", as used herein, includes autoimmune diseases, including systemic lupus erythematosus, immune thrombocytopenic purpura, rheumatoid arthritis and multiple sclerosis, rejection against allogeneic or xenogeneic organs, tissues or cells, including autologous or allogeneic transplants, graft-versus-host diseases, and anti-drug antibody responses.

In other embodiments, the antibody of the present disclosure inhibits anti-drug antibody formation. "Anti-drug antibody (ADA) response" refers to a phenomenon in which, when a specific drug, for example, a therapeutic antibody such as Humira (Abbott), is administered to a subject, an antibody against the drug in the subject is produced and weakens or destroys the efficacy of the therapeutic antibody. It was shown that when Humira was administered to patients, the ADA was produced in about 28% of the patients and the therapeutic effect of Humira appeared in 34% of ADA-negative patients but only 4% of ADA-positive patients (Bartelds et al. JAMA 2011; 305:1460-1468).

Thus, the anti-CD154 antibody according to the present disclosure, when used in combination with this therapeutic antibody, can inhibit the production of an anti-drug antibody, thereby enhance the therapeutic effect of the therapeutic antibody. In addition, in the case of biodrugs such as Darbepoetin alpha, Interferons, Anakinra, Recombinant FVIII or IX, Alglucosidase alfa and the like, the occurrence rate of the ADA reaches 3 to 89% (Chirmule et al. AAPS J. 2012; 14:296-302), and the anti-CD154 antibody of the present disclosure can also be effectively used to enhance the therapeutic effects of such drugs.

In one embodiment of the present disclosure, the antibody of the present disclosure is particularly highly effective for treatment of symptoms or diseases that are highly dependent on antibody-mediated immune responses. The antibody of the present disclosure can be effectively used to inhibit the production of an antibody against an antibody drug such as Enbrel or Humira, which is known to be highly dependent on such antibody-mediated immune responses.

In another embodiment, the antibody of the present disclosure can be effectively used for the control, treatment or prevention of autoimmune diseases such as systemic lupus erythematosus, immune thrombocytopenic purpura and the like, known as diseases highly dependent on antibody-mediated immune responses.

As used herein, the term "treatment" means delaying the progression of T cell-mediated or antibody-mediated immune disorders or diseases or inhibiting, alleviating or eliminating the physiological changes or symptoms caused by the diseases, by administering the antibody or composition of the present disclosure to mammals.

As used herein, the term "prevention" means preventing the onset of T cell-mediated or antibody-mediated immune disorders or diseases, or delaying the onset of the diseases compared to to when the antibody or composition of the present disclosure is not administered, by administering the antibody or composition of the present disclosure to mammals.

Accordingly, the antibody or fragment thereof according to the present disclosure, or a composition containing the same, may be administered to subjects who developed the disease, or subjects who are at high risk of developing the disease, or subjects in need of prevention of the disease.

As used herein, the term "subject" includes humans, non-human primates and other mammals, and particularly means subjects or patients in need of treatment or prevention of T cell-mediated or antibody-mediated immune diseases.

The effective dose and administration period of the polypeptide or fragment thereof according to the present disclosure, or a pharmaceutical composition containing the same as an active ingredient, may vary depending on a desired therapeutic effect in view of the particular patient, the kind of antibody contained in the composition, the mode of administration, and the like, and should not be toxic to the patient. The actual dose of the composition for each patient should be selected depending on various factors, including the activity of the composition used, the route of administration, the time of administration, secretion rate, other drugs used concurrently, the patient's sex, age, weight, general health condition, the underlying disease, and the like. In one embodiment, the antibody of the present disclosure may be administered for the treatment or prevention of diseases in an amount of about 1 to 100 mg/kg weight, for example, about 10, 20, 30, 40 or 50 mg/kg weight, and in some cases, administered in an amount of at most about 100 mg/kg.

The antibody or fragment thereof according to the present disclosure, or a pharmaceutical composition containing the same as an active ingredient, may be administered at suitable intervals (daily, weekly or monthly intervals) depending the half-life of the antibody administered.

The antibody of the present disclosure may be used in combination with conventional immunomodulators known in the art in order to control T cell-modulated or antibody-mediated immune diseases. For example, in the case of islet transplantation or organ transplantation, the antibody of the present disclosure may be used in combination with MD-3 (an antibody against ICAM-1; see the disclosure of Korean Patent No. 1434029), Tacrolimus, Rapamycin, Mycophenolate mofetil, or the like.

In this regard, the present disclosure is also directed to a method for the treatment or prevention of T cell-mediated or antibody-mediated immune diseases or symptoms, including autoimmune diseases, including systemic lupus erythematosus, immune thrombocytopenic purpura, rheumatoid arthritis and multiple sclerosis, rejection against transplantation of organs or tissues, including islet, kidney, heart and skin, or graft-versus-host diseases, the method comprising a step of administering the antibody or fragment thereof according to the present disclosure, or a composition containing the same, to a subject in need of treatment or prevention of the T cell-mediated or antibody-mediated immune diseases or symptoms.

In another aspect, the present disclosure is also directed to a method for inhibiting anti-drug antibody production, or a method for controlling or inhibiting antibody-mediated immune responses, or a method for inhibiting CD154-dependent T cell-mediated immune responses, or the method comprising a step of administering a therapeutically effective amount of the polypeptide, antibody or antigen-binding fragment thereof, or chimeric antibody according to the present disclosure, which specifically recognizes CD154, to a subject, a cell or a tissue.

In the method according to the present disclosure, the antibody or composition used, T cell-mediated or antibody-mediated immune diseases, the method of administration, the dose of the antibody or composition, and the subject, are as described above.

In the method according to the present disclosure, the antibody may be used in combination with an immunosuppressant in order to treat or prevent T cell-mediated or antibody-mediated immune diseases.

In other words, the method according to the present disclosure may further contain, in to addition to the antibody or fragment thereof according to the present disclosure, a component required for the treatment or prevention of T cell-mediated or antibody-mediated immune diseases.

However, even if the immunomodulators are used in combination with the antibody of the present disclosure, the kind and amount of immunomodulators used may be reduced, or the use of the immunomodulators may not be required after a certain period.

As described above, the polypeptide according to the present disclosure, which specifically recognizes CD154, can effectively inhibit the interaction of CD154 with CD40, thereby inhibiting both T cell activation and antibody production.

Therefore, in another aspect, the present disclosure also provides a kit for inhibiting anti-drug antibody production, or a kit for inhibiting antibody-mediated immune responses, or a kit for inhibiting CD154-dependent T cell-mediated immune responses, the kit comprising the polypeptide, antibody or antigen-binding fragment thereof, or chimeric antibody according to the present disclosure, which specifically recognizes CD154. For the component included in the kit according to the present disclosure, reference may be made to the above description. The kit according to the present disclosure may be used in various applications that require inhibition of antibody-mediated immune responses such as anti-drug antibody production, or inhibition of CD154-dependent T cell-mediated immune responses.

For the CD154 binding polypeptide, the mode of administration, and the like, which are used in the method of the present disclosure, reference may be made to the above description.

Hereinafter, the present disclosure will be described in further detail with reference to examples. It will be obvious to a person skilled in the art that these examples are for illustrative purposes only and are not intended to limit the scope of the present disclosure.

EXAMPLES

Example 1: Animal Test

Cynomolgus macaque monkeys (*Macaca fascicularis*) were maintained in the Nonhuman Primate Center of the Seoul National University Hospital (Seoul, Korea) or in the Korea Institute of Toxicology (Jeongeup-si, Jeollabuk-do, Korea). The monkeys used in the test were 30 to 40 months old and weighed 2.5 to 3.5 kg. A portion of this study was conducted in accordance with the guideline of the National Institutes of Health under the approval of the Institutional Animal Care and Use Committees (IACUC) of the Seoul National University Hospital, and a portion of this study was conducted in accordance with the guideline of the National Institutes of Health by the Korea Institute of Toxicology by the request of the Seoul National University.

Example 2: Production of Anti-Human CD154 Antibody

To produce an anti-human CD154 antibody, recombinant human soluble CD154 protein (sCD40L, Catalog Number: 310-02, Peprotech, N.J., USA) was immunized into BALB/c mice. One hundred µg of the protein emulsified in adjuvant (complete Freund's adjuvant for first dose, and incomplete Freund's adjuvant for second and third doses) was administered intraperitoneally to female Balb/c mice (6-8-week-old, 17-25 g; KOATECH, Pyeongtaek-si, Gyeonggi-do, Korea) three times at 2-week intervals. At two weeks after final immunization, 100 µg of CD154 protein was injected intraperitoneally to the immunized mice, and after 3 days, the spleens were extracted from the mice, and splenocytes were isolated therefrom.

For production of a monoclonal antibody, $10^8$ splenocytes were fused with $10^7$ SP2/0-Ag14 mouse myeloma cells (ATCC® CRL-1581; American Type Culture Collection, Manassas, Va., USA) resistant to 9-azaguanine by use of 50% polyethylene glycol 4000 (Roche, Basel, Switzerland) (Koeler and Milstein, Nature 1975; 256: 495-497).

After fusion, the cells were washed once with PBS, and then resuspended in DMEM (Dulbecco's modified Eagle's medium) containing 20% fetal bovine serum, 100 µM hypoxanthine, 0.44 µM aminopterin and 16 µM thymidine (HAT medium, Sigma). Next, the cells were inoculated into four 96-well plates, and cultured under the conditions of 37° C. and 5% $CO_2$ for 2 weeks until colonies were formed. Next, the medium was collected from each well, and whether the antibody would be produced by the cells was screened using Jurkat D1.1 cells transfected with the human CD154 gene (ATCC® CRL-10915). The collected medium was incubated with Jurkat D1.1 cells at 4° C. for 30 minutes, and then washed with PBS containing 0.05% Tween after which it was incubated with FITC-conjugated anti-mouse IgG antibody (BD Bioscience, San Jose, Calif., USA) at 4° C. for 30 minutes, and colonies showing positive staining for Jurkat D1.1 were selected.

Meanwhile, a negative control group was stained only with FITC-conjugated anti-mouse IgG antibody. The selected colonies were dispensed into each well of 96-well plates at a density of 0.5 cells per well and subcloned using a limiting dilution, thereby obtaining hybridoma clones producing the antibody. Among the obtained hybridomas, a clone producing a mouse antibody that binds to human CD154 was selected and named "RD-05" (see FIG. 1).

Using CD154-transfected Jurkat D1.1 cells, the binding affinity of the antibody produced as described above was measured by flow cytometry using FACSAria™ (Becton Dickinson, San Jose, Calif., USA) according to the manufacturer's instructions. As can be seen in FIG. 1, the Jurkat D1.1 cells stained with the FITC-conjugated anti-mouse IgG secondary antibody after incubation with the RD-05 mouse antibody showed a positive response, unlike the negative control group stained only with the secondary antibody.

Example 3: Sequencing of the Variable Region of Anti-Human CD154 Antibody

In order to determine the sequences of the CDRs of the heavy chain and light chain (comprising a heavy-chain variable region ($V_H$) and a light-chain variable region ($V_L$), respectively) of the above-described RD-05 antibody, the genes were cloned as follows:

For cloning of the genes, RNA was extracted from the RD-05 hybridoma cells using an RNA MiniPrep kit (Qiagen, Hilden, Germany) according to the manufacturer's instructions, and subjected to PCR (Novagen® Mouse Ig primer set #69831, MuIgV$_H$5'-F, MuIgGV$_H$3'-2 and MuIgκV$_L$5'-B, MuIgκV$_L$3'-1), thereby synthesizing cDNA.

Primers and PCR conditions for synthesis of heavy-chain cDNA used are as follows: forward primer MuIgV$_H$5'-F: 5'-ACTAGTCGACATGAACTTYGGGYTSAGMTT-GRTTT-3' (SEQ ID NO:23) (Y: C or T; S: C or G; M: A or C; and R: A or G); reverse primer MuIgGV$_H$3'-2: 5'-CC-CAAGCTTCCAGGGRCCARKGGATARACIGRTGG-3' (SEQ ID NO:24) (R: A or G; K G or T; and I: inosine); PCR conditions: 94° C. for 4 min; 35 cycles, each consisting of 94° C. for 45 sec, 52° C. for 45 sec, and 72° C. for 1 min; 72° C. for 7 min; stop at 4° C.

Next, the PCR product was cloned into a pGEM®-T easy vector using a TA Cloning™ kit (Promega) according to the manufacturer's instructions. Next, in order to find the mouse heavy-chain variable region, protein displays in using IMGT Repertoire (IG and TR) of IMGT (the international ImMunoGeneTics information system http//:imgt.cines.fr) were performed, thereby finding framework 1 from which the heavy-chain variable region of RD-05 starts. Next, standard PCR for determining the gene sequence of the full-length heavy chain of RD-05 was performed under the following conditions: annealing at 55° C. for 1 min; 95° C. for 5 min; 37 cycles, each consisting of 95° C. for 1 min, 55° C. for 1 min, and 72° C. for 1 min; 72° C. for 5 min; and stop at 4° C. The primers used in the PCR were as follows: forward primer 5'-CTCGAGATGAGGGTGTTAAT-TCTTTTGTGGCTGTTTACA-3' (SEQ ID NO:25); and reverse primer 5'-GCCCTTGGTGGAAGCAGATGA-GACGGTAACCGTGGTCCC-3' (SEQ ID NO:26). Next, the PCR product was cloned into a pGEM®-T easy vector using a TA Cloning™ kit, and the sequences of the identified CDR regions were determined using IMGT/V-QUEST. As a result, it was found that the sequences of heavy-chain variable region HCDR1, HCDR2 and HCDR3 are represented by SEQ ID NOs: 1 to 3, respectively: SEQ ID NO:1: GYSITSDYA; SEQ ID NO:2: ITYSGTT; and SEQ ID NO:3: ARSPYYGPWYFDV. The amino acid sequence and nucleic acid sequence of the heavy-chain variable region are represented by SEQ ID NOs: 7 and 17, respectively.

Primers and PCR conditions for synthesis of light-chain cDNA were as follows: forward primer MuIgκV$_L$5'-B: 5'-GGGAATTCATGGAGACAGACACACTCCTGCTAT-3' (SEQ ID NO:27); reverse primer MuIgκV$_L$3'-1: 5'-CC-CAAGCTTACTGGATGGTGGGAAGATGGA-3' (SEQ ID NO:28); PCR conditions: 94° C. for 4 min; 35 cycles, each consisting of 94° C. for 45 sec, 52° C. for 45 sec, and 72° C. for 1 min; 72° C. for 7 min; and stop at 4° C.

The light-chain gene of RD-05 was cloned into a pGEM-T easy vector. Next, in order to find a mouse immunoglobulin variable region, protein displays in IMGT Repertoire (IG and TR) were performed, thereby finding framework 1 from which the light-chain variable region of RD-05 starts. Next, standard PCR for determining the gene sequence of the full-length light chain of RD-05 was performed under the following conditions: 95° C. for 5 min; 37 cycles, each consisting of 95° C. for 1 min, 55° C. for 1 min, and 72° C. for 1 min; 72° C. for 5 min; stop at 4° C. The primers used in the PCR were as follows: forward primer 5'-CTCGAGATGGAGACAGATACACTTTTGC-TATGGGTTCTG-3' (SEQ ID NO:29); and reverse primer 5'-CTGGTGCCGCCACAGTCCGTTTAATTTCCAGCT-TAGTCCC-3' (SEQ ID NO:30). Next, the PCR product was cloned into a pGEM®-T easy vector using a TA cloning kit, and then the sequences of the identified CDR regions were determined using IMGT/V-QUEST. As a result, the sequences of light-chain variable region LCDR1, LCDR2 and LCDR3 are represented by SEQ ID NOs: 4 to 6, respectively. SEQ ID NO:4: QSVDYDGDSY; SEQ ID NO:5: AAS; and SEQ ID NO:6: QQSNEDP. The amino acid sequence and nucleic acid sequence of the light-chain variable region are represented by SEQ ID NOs: 8 and 21, respectively.

Example 4: Determination of CD154 Antigen Epitope Recognized by Anti-Human CD154 Antibody Conjugates of a total of three CD154 antigen peptide portions and ovalbumin were constructed by Peptron (Daejeon, Korea). As a positive control, recombinant human CD154-Fc fusion protein (Adipogen, Incheon, Korea) was used. Each peptide-ovalbumin conjugate and CD154 antigen were subjected to 10% SDS-PAGE, and then subjected to Western blotting with the mouse RD-05 antibody. FIG. 2 shows the results of the Western blotting. In FIG. 2, lane 1 is recombinant CD154 protein; lane 2 is ovalbumin-SPGR-FERILLRA (SEQ ID NO:37); lane 3 is ovalbumin-GRFER-ILLRA (SEQ ID NO:34); and lane 4 is ovalbumin-SPG RFERILLR (SEQ ID NO:36). The epitope determined in this Example is a CD40 ligand portion composed of the amino acids at residues 197 to 208 of SEQ ID NO:22. As mentioned above, the determined epitope is included in the second hydrophilic region that comes into contact with CD40, and in the charge interaction region that interacts with CD40. Therefore, it can be considered that the epitope that is recognized by the antibody constructed herein comprises the whole or a part of the second hydrophilic region and the charge interaction region. In this regard, the epitope according to the present disclosure may comprise G199, R200 and R203 of the second hydrophilic region as identified herein, and may further comprise any one or more of Q232 of the second hydrophilic region and R207 or E230 of the charge interaction region.

Example 5: Construction of Human IgG4 Chimeric Anti-Anti CD154 Antibodies

For cloning of the variable region genes of the antibody produced as described above, RNA was extracted from RD-05 hybridoma cells using an RNA MiniPrep kit (Qiagen) according to the manufacturer's instructions, and then subjected to PCR (Novagen® Mouse Ig primer set #69831, MuIgV$_H$5'-F, MuIgGV$_H$3'-2 and MuIgκV$_L$5'-B, MuIgκV$_L$3'-1), thereby synthesizing variable region cDNA. Primers and PCR conditions for synthesis of heavy-chain variable region cDNA were as follows: forward primer MuIgV$_H$5'-F: 5'-ACTAGTCGACATGAACTTYGGGYT-SAGMTTGRTTT-3' (Y: C or T; S: C or G; M: A or C; and R: A or G) (SEQ ID NO:23); reverse primer MuIgGV$_H$3'-2: 5'-CCCAAGCTTCCAGGGRCCARKGGATARACI-GRTGG-3' (SEQ ID NO:24); (R: A or G; K: to G or T; and I: inosine); PCR conditions: 94° C. for 4 min; 35 cycles, each consisting of 94° C. for 45 sec, 52° C. for 45 sec, and 72° C. for 1 min; 72° C. for 7 min; stop at 4° C. Primers and PCR conditions for synthesis of light-chain variable region cDNA were as follows: forward primer MuIgκV$_L$5'-B: 5'-GGGAATTCATGGAGACAGACACACTCCTGCTAT-3' (SEQ ID NO:27); reverse primer MuIgκV$_L$3'-1: 5-CC-CAAGCTTACTGGATGGTGGGAAGATGGA-3' (SEQ ID NO:28); PCR conditions: 94° C. for 4 min; 35 cycles, each consisting of 94° C. for 45 sec, 52° C. for 45 sec, and 72° C. for 1 min; 72° C. for 7 min; stop at 4° C.

After cDNAs were synthesized by the first PCR as described above, a sequence from which the VH region starts was found in IMGT. Next, the variable regions of RD-05 were amplified using the following primers:

RD-05 V$_H$ region forward primer: 5'-CTCGAGAT-GAGGGTGTTAATTCTTTTGTGGCTGTTTACA-3' (SEQ ID NO:25); RD-05 V$_H$ region reverse primer: 5'-GCCCTTGGTGGAAGCAGATGA-GACGGTAACCGTGGTCCC-3' (SEQ ID NO:26); RD-05 V$_L$ region forward primer: 5'-CTCGAGATGGAGACAGA-TACACTTTTGCTATGGGTTCTG-3' (SEQ ID NO:29), RD-05 V$_L$ region reverse primer: 5'-CTGGTGCCGC-CACAGTCCGTTTAATTTCCAGCTTAGTCCC-3' (SEQ ID NO:30). The PCR was performed under the following conditions: 94° C. for 4 min; 35 cycles, each consisting of 94° C. for 45 sec, 52° C. for 45 sec, and 72° C. for 1 min; 72° C. for 7 min; stop at 4° C.

For cloning of human IgG4 gene, total RNA was first extracted from human peripheral blood monocytes using an RNeasy mammalian total RNA MiniPrep kit (Qiagen) according to the manufacturer's instructions, and then subjected to reverse transcription PCR using nucleotide sequence-specific primers and reverse transcriptase, thereby synthesizing cDNA. As the primers for cDNA synthesis, human IgG4 heavy-chain nucleotide sequence-specific primers (forward to primer: 5'-GTTACCGTCT-CATCTGCTTCCACCAAGGGCCCCTCCGTG-3' (SEQ ID NO:42); and reverse primer: 5'-GAATTCTCAT-TTGCCCAGGCTCAGGGACAGGGACTTCTG-3') (SEQ ID NO:43) or human kappa light-chain nucleotide sequence-specific primers (forward primer: 5'-CTGGAAAT-TAAACGGACTGTGGCGGCACCATCCGTTTTT-3' (SEQ ID NO:44); and reverse primer: 5'-GAATTCTCAA-CATTCGCCCCTGTTAAAGCTTTTTGTGAC-3' (SEQ ID NO:45) were used. The PCR was performed under the following conditions: 94° C. for 4 min; 35 cycles, each consisting of 94° C. for 45 sec, 52° C. for 45 sec, and 72° C. for 1 min; 72° C. for 7 min; stop at 4° C.

Overlap PCR for fusing the heavy-chain variable region and the human IgG4 constant region, and overlap PCR for fusing the light-chain variable region and the human light-chain kappa region, were performed using the following primers:

RD-05 $V_H$ region forward primer: 5'-CTCGAGAT-GAGGGTGTTAATTCTTTTGTGGCTGTTTACA-3' (SEQ ID NO: 25); human IgG4 constant region $C_H$ region reverse primer: 5'-GAATTCTCAT-TTGCCCAGGCTCAGGGACAGGGACTTCTG-3' (SEQ ID NO:43); RD-05 $V_L$ region forward primer: 5'-CTCGAGATGGAGACAGATACACTTTTGC-TATGGGTTCTG-3' (SEQ ID NO:29); human light-chain kappa $C_L$ region reverse primer: 5'-GAATTCTCAACAT-TCGCCCCTGTTAAAGCTTTTTGTGAC-3' (SEQ ID NO:45). The overlap PCR was performed under the following conditions: 94° C. for 4 min; 35 cycles, each consisting of 94° C. 1 min, 61° C. for 1 min, and 72° C. for 1 min; 72° C. for 5 min; stop at 4° C.

In addition, an RD-05 mutant antibody [RD-05 (L115E)] wherein leucine at residue 115 of the heavy-chain constant region of human IgG4 was substituted with glutamic acid (L115E) was produced in the following manner. Specifically, a gene comprising the heavy-chain variable region and proximal heavy-chain constant region including overlapping 11 amino acids encompassing residue 115 of the human IgG4 constant region was amplified by PCR, and the remaining distal heavy-chain constant region including overlapping 11 amino acids encompassing residue 115 was amplified by PCR, followed by overlap PCR The PCR amplification reactions were performed using the following primers: RD-05 $V_H$ region forward primer: 5'-CTCGAGAT-GAGGGTGTTAATTCTTTTGTGGCTGTTTACA-3' (SEQ ID NO:25); human IgG4 constant 115 region $C_H$ reverse primer: 5'-CAGGAACACGGAAGGTCCGCCTTCAAAT-TCAGGGGCAGG-3' (SEQ ID NO:46); human IgG4 constant 115 region $C_H$ forward primer: 5'-CCCTGCCCTGCCCCTGAATTT-GAAGGCGGACCTTCCGTG-3' (SEQ ID NO:47); and human IgG4 constant region $C_H$ reverse primer: 5'-GAAT-TCTCATTTGCCCAGGCTCAGGGACAGGGACTTCTG-3' (SEQ ID NO:43). The PCR amplification reactions were performed under the following reactions: 94° C. for 4 min; 35 cycles, each consisting of 94° C. for 1 min, 61° C. for 1 min, and 72° C. for 1 min; 72° C. for 5 min; stop at 4° C.

The overlap PCR was performed using the following primers: RD-05 $V_H$ region forward primer: 5'-CTCGAGAT-GAGGGTGTTAATTCTTTTGTGGCTGTTTACA-3' (SEQ ID NO:25); human IgG4 constant region $C_H$ reverse primer: 5'-GAATTCTCAT-TTGCCCAGGCTCAGGGACAGGGACTTCTG-3' (SEQ ID NO:43). The overlap PCR was performed under the same conditions as used in the PCR amplification. The heavy-chain and light-chain chimeric genes were cloned into pGEM®-T easy vector using a TA cloning kit, and then sequenced.

In the case of the heavy-chain chimeric gene, it was inserted into pCDNA3.3™ mammalian expression vector (Invitrogen), and the cloning product was digested with XhoI/EcoRI, while the light-chain chimeric gene was cloned into pOptiVEC™ (Life Technologies, Gaithersburg, Md., USA) vector and the cloning product was digested with XhoI/EcoRI (FIG. 4). Then, the vector constructs were sequenced).

For transfection, DHFR-negative CHO-DG44 cells (Invitrogen) were used. The cells were cultured in α-MEM medium containing 7% fetal bovine serum (Gibco, Grand Island, N.Y., USA), ribonucleoside and deoxyribonucleoside. The CHO-DG44 cells were transfected with pCDNA3.3™ and pOptiVEC™ vectors using Effectene™ (Qiagen) transfection reagent. One day before transfection, the CHO-DG44 cells were seeded into a 6-well plate containing 2 ml of medium at a concentration of 2×10$^5$ cells/ml. For transfection, 10 μl of Effectene™ transfection reagent was added to a DNA-enhancer mixture (0.4 μg plasmid in 100 μl EC buffer and 3.2 μl enhancer). The mixture of the plasmid DNA and the Effectene™ transfection reagent solution was added to the CHO-DG44 cells cultured overnight as described above, followed by incubation at 37° C. After 3 days of culture, the supernatant was analyzed by ELISA.

Stably transfected cells were selected in fetal bovine serum (FBS)-supplemented α-MEM medium free of ribonucleoside and deoxyribonucleoside. The medium free of ribonucleoside and deoxyribonucleoside blocks the growth of DHFR-deficient cells. The selected cells were adapted in FBS-free PowerCHO™2 media (Lonza, Walkersville, Md., USA) in the presence of 400 μg/ml G418 for supporting the growth of heavy chain-expressing cells and in the presence of 1,000 nM methotrexate (MTX) for supporting the growth of light chain-expressing cells. Next, the cells were cultured in a 100-mm dish for 10 days or more, and then single colonies were harvested and transferred to a 96-well plate including FBS-free PowerCHO™2 media. Cells producing the antibody were screened, and then subcloned three times, and cells producing as high concentration of the antibody were cultured in PowerCHO™2 media in an Erlenmeyer flask at a concentration of 4×10$^5$ viable cells/ml. After adaptation, the antibody was isolated and purified from the supernatant using protein G column.

Using CD154-transfected Jurkat D1.1 cells, the binding affinities of the IgG4 and IgG4 (L115E) RD-05 chimeric antibodies produced as described above were compared by flow cytometry using FACSAria™ (Becton Dickinson) according to the manufacturer's instructions. As can be seen in FIG. 5, the Jurkat D1.1 cells stained with the FITC-conjugated anti-human immunoglobulin second antibody after incubation with the IgG4 or IgG4 (L115E) RD-05 chimeric antibody showed a positive response, unlike the negative control stained only with the secondary antibody.

Example 6: Determination of Affinities of Anti-Human CD154 Antibodies for Antigen The binding affinity $K_D$ of each of the RD-05 mouse antibody and IgG4 and IgG4 (L115E) RD-05 chimeric antibodies, produced as described above, for human CD154 antigen, was measured using an SPR method by Woojung BSC, Inc. (Suwon, Gyeonggi-do, Korea). Specifically, 17.5 μg/ml of recombinant human CD154 protein in immobilization buffer (10 mM sodium acetate, pH 6.0) was attached to a CMDH gold chip (Cat #13206066, Reichert Technologies, Depew, N.Y., USA) at a density of 2300 RU (resonance unit; 1 RU=1 pg/mm$^2$ surface area), after which 3.125 μg/ml of bovine serum albumin was attached at a density of 650 RU. The RD-05 antibody was diluted in PBS at 0.3125, 0.65, 1.25, 2.5, 5, 10, 20, 40, 80, 160, 320, 2560 and 5120 nM. Each of the antibody dilutions was run at a flow rate of 30 μl/min for an association time of 5 min and for a dissociation time of 5 min, and at the same time, data were read with a Reichert's SR7500DC system and analyzed by Scrubber 2 software to determine $K_a$ and $K_d$ values. Based on the determined values, the $K_D$ values were calculated. The $K_D$ values of the RD-05 mouse antibody and the IgG4 and IgG4 (L115E) RD-05 chimeric antibodies were shown to be $3.7 \times 10^{-8}$M, $4.5 \times 10^{-8}$M and $3.3 \times 10^{-8}$M, respectively, which are good values that do not greatly differ from the value ($1.0 \times 10^{-8}$ M) measured for a conventional 5C8 clone (Schuler et al. Transplantation 2004; 77:717-726).

Example 7: The Ability of Anti-Human CD154 Antibodies to Inhibit CD40-CD154 Interaction Five hundred ng of a CD40 fragment (abcam ab155710, UK) for ELISA capture was coated on each well of an ELISA plate (Nunc-Immuno Plate, #439454) at 4° C. overnight, and then 100 µl of 1× blocking buffer (Sigma B6429) was added to each well, followed by incubation in an incubator at 37° C. for 1 hour. Each of the RD-05 mouse antibody and IgG4 and IgG4 (L115E) RD-05 chimeric antibodies produced in the above Examples was serially diluted from a concentration of 1,000 ng/ml to a concentration 2.43 ng/ml. 500 ng of CD154-biotin (abcam ab24966) was pre-incubated with the same amount of each of the antibody dilutions at room temperature for 20 minutes, and the pre-incubated material was incubated in the above-blocked ELISA plate in an incubator at 37° C. in an amount of 100 µl/well for 1 hour. Then, the incubated plate was washed three times on an auto strip washer, and incubated with 100 µl/well of a 5000-fold dilution of streptavidin-horseradish peroxidase (Thermo, #21126) in an incubator at 37° C. for 40 minutes, and then washed three times on an auto strip washer. Next, each well of the incubated plate was incubated with 100 µl of 3,3',5,5'-tetramethylbenzidine (TMB) ELISA substrate for 20 minutes, and the reaction was stopped by addition of 100 µl of 2N $H_2SO_4$ stop solution. The absorbance at 450 nm was read using a microplate reader. As a result, as shown in FIG. 3, it could be seen that the RD-05 antibody could specifically inhibit the CD154-CD40 interaction in a concentration-dependent manner.

Example 8: Inhibitory Effect of Human IgG4 RD-05 Chimeric Antibody Against Anti-Drug Antibody Formation In order to evaluate the effect of the human IgG4 (L115E) RD-05 chimeric antibody on the inhibition of anti-drug antibody formation, Humira was injected into Cynomolgus monkeys. Specifically, 5 mg/kg of Humira was administered subcutaneously to the monkeys at 2-week intervals, and serum was collected weekly, and the concentration of anti-Humira antibody in the collected serum using a 1(9651/ TNFαblocker ADA kit (Immune Diagnostik). A test group was administered with the IgG4 (L115E) RD-05 chimeric antibody (20 mg/kg) on days −1 and 6 relative to the first day of administration of Humira. As a result, in the control group administered with Humira alone, a high concentration of anti-Humira antibody was produced, but in the test group administered with the IgG4 (L115E) RD-05 chimeric antibody, no anti-drug antibody was produced (FIG. 6; cut-off 10 AU/ml). This indicates that the IgG4 (L115E) RD-05 chimeric antibody according to the present disclosure can effectively inhibit anti-drug antibody formation.

Example 9: Effect of Human IgG4 RD-05 Chimeric Antibody on Platelet Activation In order to examine the effect of the human IgG4 RD-05 chimeric antibody on platelet activation, human CD32a-transgenic mice (Jackson Lab., Bar Harbor, Me., USA), were used. When such mice are injected with a complex of human CD154 antigen and the anti-human CD154 antibody, the number of platelets greatly decreases within 10 minutes, and thus the side effect of thrombus formation caused by the anti-CD154 antibody can be evaluated (Robles-Carrillo et al. J Immunol. 2010; 185:1577-1583). A mixture of 50 µM recombinant human soluble CD154 protein and the human IgG4 or IgG4 (L115E) RD-05 chimeric antibody was injected into the tail vein of human CD32a-transgenic mice, and after 10 minutes, blood was collected from the heart, and the number of platelets in the blood was measured. As a result, as shown in FIG. 7, the number of platelets in the mice administered with the IgG4 RD-05 antibody decreased compared to that in the nominal control group. However, the number of platelets in the mice administered with the IgG4 (L115E) RD-05 chimeric antibody did not differ from that in the nominal control group. This suggests that the human IgG4 (L115E) RD-05 chimeric antibody does not cause the side effect of platelet activation.

In summary, in the present disclosure, the antibody (RD-05) capable of inhibiting the CD154-CD40 interaction by binding to the human CD154 protein was developed, and it was found that the affinity of the antibody (RD-05) for the human CD154 antigen does not significantly differ from that of a conventional anti-CD154 antibody (5C8 clone).

Furthermore, when the IgG4 (L115E) RD-05 chimeric antibody was administered to Cynomolgus monkeys, it very effectively inhibited the formation of an anti-drug antibody against Humira, indicating that the chimeric antibody can inhibit antibody-mediated immune responses.

In addition, an immune complex of human CD154 protein and the anti-CD154 antibody was injected intravenously into CD32A-transgenic mice, and after 10 minutes, blood was collected from the heart, and the number of platelets in the blood was measured. As a result, the number of platelets in the mice administered with the IgG4 RD-05 chimeric antibody decreased. However, the number of platelets in the mice administered with the IgG4 (L115E) RD-05 chimeric antibody did not differ from that in the normal control group. This suggests that the human IgG4 (L115E) RD-05 chimeric antibody according to the present disclosure does not cause the side effect of platelet activation.

Although the exemplary embodiments of the present disclosure have been described in detail above, those skilled in the art will appreciate that the scope of the present disclosure is not limited to these embodiments and that various modifications and improvements also fall within the scope of the present disclosure as defined in the appended claims.

Unless otherwise defined, all technical terms used herein have the same meaning as commonly understood by one of ordinary skill in the art to which the present invention pertains. The contents of all the publications referred to herein are incorporated herein by reference.

What is claimed is:

1. A CD154 binding polypeptide comprising a HCDR (Complementary Determining Region) 1, 2 and 3 from a immunoglobulin heavy chain variable region (VH); and LCDR 1, 2 and 3 from a immunoglobulin light chain variable region (VL),
   wherein the HCDR1 has a sequence set forth in SEQ ID NO: 1; the HCDR2 has a sequence set forth in SEQ ID NO: 2 and the HCDR3 has a sequence set forth in SEQ ID NO: 3; and the LCDR1 has a sequence set forth in SEQ ID NO: 4, the LCDR2 has a sequence set forth in SEQ ID NO: 5 and the LCDR3 has a sequence set forth in SEQ ID NO: 6.

2. The polypeptide of claim 1, wherein the polypeptide binds to a CD154 from a human, Rhesus or Cynomolgus CD154.

3. The polypeptide of claim 1, wherein the polypeptide specifically recognizes a CD154 sequence set for the in SEQ ID NO: 12 or 13.

4. The polypeptide of claim 1, wherein the CD154 binding peptide is an anti-CD154 antibody which comprises: a heavy-chain variable region having an amino acid sequence set forth in SEQ ID NO: 7; and a light-chain variable region having an amino acid sequence set forth in SEQ ID NO: 8.

5. The polypeptide of claim 1, wherein the CD154 binding peptide is an anti-CD154 antibody which is a monoclonal antibody, a chimeric antibody, a humanized antibody.

6. The polypeptide of claim 5, wherein the anti-CD154 antibody is a chimeric antibody, wherein the chimeric antibody comprises a variable region of non-human origin and an Fc region of human origin.

7. The polypeptide of claim 6, wherein the Fc region is an IgG4 Fc, wherein the IgG4 Fc comprises a leucine-to-glutamic acid substitution (L115E) at an amino acid residue corresponding to residue 115 of SEQ ID NO: 9.

8. The polypeptide of claim 1, wherein the CD154 binding peptide is an anti-CD154 antibody which is a multimeric antibody, a heterodimeric antibody, a hemidimeric dimer, a multivalent antibody or a single-chain antibody.

9. The polypeptide of claim 1, wherein the CD154 binding peptide is an anti-CD154 antibody which is conjugated with a substance selected from the group consisting of therapeutic agents, prodrugs, peptides, proteins, enzymes, viruses, lipids, biological modifiers, drugs and Polyethylene glycol.

10. The polypeptide of claim 4, wherein the antibody further comprises: a heavy-chain constant region of SEQ ID NO: 9 or SEQ ID NO: 10; and a light-chain constant region of SEQ ID NO: 11.

11. A polynucleotide encoding the polypeptide according to claim 4.

12. A vector comprising the polynucleotide according to claim 11.

13. A composition for inhibiting an anti-drug antibody production, comprising the CD154 binding polypeptide according to claim 1.

14. A pharmaceutical composition for treating T cell-mediated or antibody-mediated immune diseases or symptoms, the pharmaceutical composition comprising the CD154 binding polypeptide according to claim 1.

15. The pharmaceutical composition of claim 14, wherein the T cell-mediated or antibody-mediated immune disease or symptom is an anti-drug antibody response, an autoimmune disease including systemic lupus erythematosus, immune thrombocytopenic purpura, rheumatoid arthritis and multiple sclerosis, a rejection against transplantation of organs or tissues including islet, kidney, heart and skin, or a graft-versus-host disease.

16. The pharmaceutical composition of claim 15, wherein the pharmaceutical composition is for treating antibody-mediated immune diseases or symptoms, wherein the antibody-mediated immune diseases are anti-drug antibody reactions, systemic lupus erythematosus, or immune thrombocytopenic purpura.

* * * * *